US007109171B2

(12) United States Patent
Garnick et al.

(10) Patent No.: US 7,109,171 B2
(45) Date of Patent: Sep. 19, 2006

(54) METHODS FOR TREATING FSH RELATED CONDITIONS WITH GNRH ANTAGONISTS

(75) Inventors: Marc B. Garnick, Brookline, MA (US); Paul M. Martha, Jr., Topsfield, MA (US); Christopher J. Molineaux, San Mateo, CA (US); Alex DePaoli, Santa Barbara, CA (US)

(73) Assignee: Praecis Pharmaceuticals Inc., Waltham, MA (US)

( * ) Notice: Subject to any disclaimer, the term of this patent is extended or adjusted under 35 U.S.C. 154(b) by 198 days.

(21) Appl. No.: 09/793,669

(22) Filed: Feb. 28, 2001

(65) Prior Publication Data

US 2002/0058035 A1 May 16, 2002

Related U.S. Application Data

(60) Provisional application No. 60/238,337, filed on Oct. 5, 2000, provisional application No. 60/238,338, filed on Oct. 5, 2000, provisional application No. 60/185,573, filed on Feb. 28, 2000, and provisional application No. 60/185,574, filed on Feb. 28, 2000.

(51) Int. Cl.
*A61K 38/00* (2006.01)

(52) U.S. Cl. .............................. 514/15; 514/2; 530/313; 530/328; 530/398

(58) Field of Classification Search ................ 514/2, 514/15; 530/313, 328, 398, 397
See application file for complete search history.

(56) References Cited

U.S. PATENT DOCUMENTS 5,470,947 A   11/1995   Folkers et al.
5,821,230 A * 10/1998   Jiang et al.
5,843,901 A   12/1998   Roeske
5,968,895 A   10/1999   Gefter et al.

FOREIGN PATENT DOCUMENTS

WO    WO 97/44037 A1    11/1997

OTHER PUBLICATIONS

Cook et al. 2000, The Oncologist vol. 5, pp. 162–168.*
Behre, H.M. et al. "Sustained suppression of serum LH, FSH and testosterone and increase of high–density lipoprotein cholesterol by daily injections of the GnRH antagonist cetrorelix over 8 days in normal men" *Clinical Endocrinology* 40:241–248 (1994).
Menon, M. et al. "Abarelix (PPI–149), a Novel and Potent GnRH Antagonist, Induces a Rapid and Profound Reduction in Testosterone and PSA in Advanced Prostate Cancer of Patients (PrCa)" *Journal of Urology* 159(5 Suppl.):334 (May 1998).
Newling, D. "PIN I–III: When Sould We Interfere?" *European Urology* 35:504–507 (1999).

Ahokoski, O. et al. "Biological day–to–day variation and daytime changes of testosterone, follitropin, lutropin and oestradiol–17beta in healthy men" Clinical Chemistry and Laboratory Medicine 36(7):485–91 (1998).
Albertsson–Wikland, K. et al. "Twenty–four–hour profiles of luteinizing hormone, follicle–stimulating hormone, testosterone, and estradiol levels: a semilongitudinal study throughout puberty in healthy boys" Journal of Clinical Endocrinology and Metabolism 82(2):541–9 (1997).
Bablok, I. et al. "Relationship between semen quality improvement after varicocelectomy and preoperative levels of hypophyseal and gonadal hormones" International Urology and Nephrology 29(3): 345–9 (1997).
Backer, L.C. et al. "Serum follicle–stimulating hormone and luteinizing hormone levels in women aged 35–60 in the U.S. population: the Third National Health and Nutrition Examination Survey (NHANES III, 1988–1994)" Menopause 6(1):29–35 (1999).
Ballauf, A. et al. "Serum leptin and gonadotropin levels in patiens with anorexia nervosa during weight gain" Molecular Psychiatry 4(1):71–5 (1999).
Basu, M. et al. "Pituitary, gonadal and adrenal hormones after prolonged residence at extreme altitude in man" International Journal of Andrology 20(3):153–8 (1997).
Belgorosky, A. et al. "Serum concentrations of follicle stimulating hormone and luteinizing Hormone in normal girls and boys during prepuberty and at early puberty" Journal of Endorcrinological Investigation 19(2):88–91 (1996).
Bhavnani, B.R. et al. "Biologic effects of delta–8–estrone sulfate in postmenopausal women" Journal of the Society for Gynecologic Investigation 5(3):156–60 (1998).
Bondanelli, M. et al. "Effect of delta–opioid receptor agonist deltorphin on circulating concentrations of luteinizing hormone and follicle stimulating hormone in healthy fertile women" Human Reproduction 13(5):1159–62 (1998).
Brennemann, W. et al. "Pretreatment follicle–stimulating hormone: a prognostic serum marker of spermatogenesis status in patients treated for germ cell cancer" The Journal of Urology 159(6):1942–6 (Jun. 1998).
Check, J. H. et al. "A study to determine whether serum follicle–stimulating hormone can be a marker for ovarian hyperresponse to follicle–maturing drugs for in vitro fertilization" Gynecologic and Obstetric Investigation 43(4):242–4 (1997).

(Continued)

*Primary Examiner*—B. Dell Chism
(74) *Attorney, Agent, or Firm*—Lahive & Cockfield, LLP; Giulio A. DeConti, Jr.; Maria Laccotripe Zacharakis

(57) ABSTRACT

Methods for treating FSH related conditions, such as prostatic intraepithelial neoplasia, pedophilia, infertility, or vaginal bleeding, with GnRH antagonists are disclosed. The methods of the invention generally feature administering to a subject a GnRH antagonist suitable for in vivo administration and able to reduce both plasma FSH and LH levels in a subject, in an amount or in a formulation effective to reduce plasma FSH levels in the subject to a symptom alleviating level. In vitro fertilization and male contraceptive methods are also provided.

29 Claims, 5 Drawing Sheets

OTHER PUBLICATIONS

Chia, S.E. et al. "Endocrine profiles of male workers with exposure to trichloroethylene" American Journal of Industrial Medicine 32(3):217–22 (1997).

Christin–Maitre, S. et al. "Homologous in vitro bioassay for follicle–stimulating hormone (FSH) reveals increased FSH biological signal during the mid– to late luteal phase of the human menstrual cycle" Journal of Clinical Endocrinology and Metabolism 81(6):2080–8 (1996).

Crottaz, B. et al. "Normogonadotropic primary amenorrhea in a growth hormone–deficient woman with ectopic posterior pituitary: gonadotropin pulsatility and follicle–stimulating hormone bioactivity" Journal of Endocrinological Investigation 19(1):48–53 (1996).

de Souza, C.J.H. et al. "Incipient ovarian failure associated with raised levels of follicle stimulating hormone and reduced levels of inhibin A in older sheep" Human Reporoduction 13(11):3016–22 (1998).

de Ziegler, D. et al. "Synchronization of endogenous and exogenous FSH stimuli in controlled ovarian hyperstimulation (COH)" Human Reproduction 13(3):561–4 (1998).

Demkow, T. et al. "Sperm, LH FSH, testosterone evaluation in patients with testicular cancer. Preliminary study" Ginekologia Polska 69(6):405–9 (1998).

Derksen, J.G.M. et al. "The effect of hysterectomy and endometrial ablation on follicle stimulating hormone (FSH) levels up to 1 year after surgery" Maturitas 29(2):133–8 (1998).

Dirnhofer, S. et al. "Coexpression of gonadotropic hormones and their corresponding FSH– and LH/CG–receptors in the human prostate" The Prostate 35(3):212–20 (1998).

Farhi, J. et al. "Early prediction of ovarian multifollical response during ovulation induction in patients with polycystic ovary syndrome" Fertility and Sterility 67(3):459–62 (1997).

Galtier–Dereure, F. et al. "Ovarian reserve test with the gonadotrophin–releasing hormone agonist buserelin: correlation with in–vitro fertilization outcome" Human Reporoduction 11(7):1393–8 (1996).

Gordon, W. Jr. e al. "A study of reproductive function in patients with seminoma treated with radiotherapy and orchidectomy: (SWOG–8711). Southwest Oncology Group" Interntaional Journal of Radiation Oncology, Biology, Physics 38(1):83–94 (1997).

Greenman, Y. et al. "The use of beta–subunits of gonadotrophin hormones in the follow–up of clinically non–functioning pituitary tumours" Clinical Endocrinology 49(2):185–90 (1998).

Harris, P.E. "Biochemical markers for clinically non–functioning pituitary tumours" Clinical Endocrinology 49(2):163–4 (1998).

Illingworth, P.J. et al. "Inhibin–B: a likely candidate for the physiologically important form of inhibin in men" Journal of Clinical Endocrinology and Metabolism 81.(4):1321–5 (1996).

Jensen, T.K. et al. "Inhibin B as a serum marker of spermatogenesis: correlation to differences in sperm concentration and follicle–stimulating hormone levels. A study of 349 Danish men" Journal of Clinical Endocrinology and Metabolism 82(12):4059–63 (1997).

Kerdelhue, B. et al. "Stimulatory effect of a specific substance P antagonist (RPR 100893)of the human NK1 receptor on the estradiol–induced LH and FSH surges in the ovariectomized cynomolgus monkey" Journal of Neuroscience Research 50(1): 94–103 (1997).

Komorowski, J. et al. "Effects of thyrotropin, follicle stimulating hormone and luteinizing hormone on sIL–2R in vitro secretion from human peripheral blood mononuclear cells" CYTOBIOS 93(372):43–8 (1998).

Kovcin, V.N. et al. "Serum gonadotropin levels in patients with germ–cell tumors of the testis: interrelations, possible cross–reactions and interpretation of beta–HCG level" International Journal of Biological Markers 12(2):55–60 (1997).

Kramer, S. et al. "Gonadotropin levels in ovarian cyst fluids: a predictor of malignancy?" International Journal of Biological Markers 13(3): 165–8 (1998).

Leifke, E. et al., "Does the gonadotrophic axis play a role in the pathogenesis of Sertoli–cell–only syndrome?" International Journal of Andrology 20(1):29–36 (1997).

Meriggiola, M.C. et al. "Annual patterns of luteinizing hormone, follicle stimulating hormone, testosterone and inhibin in normal men" Human Reproduction 11(2): 248–52 (1996).

Miller, P.B. et al., "Correlation of reproductive aging with function in selected organ systems" Fertility and Sterility 68(3):443–8 (1997).

Mitamura, R. et al. "Diurnal rhythms of luteinizing hormone, follicle–stimulating hormone, and testosterone secretion before the onset of male puberty" Journal of Clinical Endocrinology and Metabolism 84(1):29–37 (1999).

Morley, J.E. et al. "Longitudinal changes in testosterone, Luteinizing hormone, and follicle–stimulating hormone in healthy older men" Metabolism: Clinical and Experimental 46(4):420–3 (1997).

Mukherjee, T. et al. "An elevated day three follicle–stimulating hormone: luteinizing hormone ratio (FSH:LH) in the presence of a normal day 3 FSH predicts a poor response to controlled ovarian hyperstimulation" Fertility and Sterility 65(3):588–93 (1996).

Osuga, Y. et al. "Derivation of functional antagonists using N–terminal extracellular domain of gonadotropin and thyrotropin receptors" Molecular Endocrinology 11(11);1659–68 (1997).

Peichl, P. et al. "Association between female sex hormones and biochemical markers of bone turnover in peri– and postmenopausal women" Calcified Tissue International 62(5):388–94 (1998).

Phillips, D.J. et al. "Changes in the isoforms of luteinizing hormone and follicle–stimulating hormone during puberty in normal children" Journal of Clinical Endocrinology and Metabolism 82(9):3103–6 (1997).

Qui, Q. et al. "Total urinary follicle stimulating hormone as a biomarker for detection of early pregnancy and periimplantation spontaneous abortion" Environmental Health Perspectives 105(5): 862–6 (1997).

Reame, N.E., et al. "Net increase in stimulatory input resulting from a decrease in inhibin B and an increase in activin A may contribute in part to the rise in follicular phase follicle–stimulating hormone of aging cycling women" Journal of Clinical Endocrinology and Metabolism 83(9):3302–7 (1998).

Reimer, T. et al. "Estradiol, gonadotropins, and tumor markers in ovarian cyst fluid" Acta Obstetricia et Gynecologica Scandinavica 76(5):478–83 (1997).

Savastano, S. et al. "Changes in glycosylation pattern of circulating gonadotropins after acute administration of gonadotropin–releasing hormone in patients with anorexia nervosa" European Journal of Endocrinology 138(1):76–81 (1998).

Schipper, L. et al. "Lack of correlation between maximum early follicular phase serum follicle stimulating hormone concentrations and menstrual cycle characteristics in women under the age of 35 years" Human Reproduction 13(6):1442–8 (1998).

Sugahara, T. et al. "Expression of biologically active fusion genes encoding the common alpha subunit and either the CG beta or FSH beta subunits: role of a linker sequence" Molecular and Cellular Endocrinology 125(1–2):71–7 (1996).

Suvisaari, J. et al. "Pharmacokinetics and pharmacodynamics of 7alpha–methyl–19–nortesto–sterone after intramuscular administration in healthy men" Human Reproduction 12(5):967–73 (1997).

Taylor, A.E. et al. "A randomized, controlled trial of estradiol replacement therapy in women with hypergonadotropic amenorrhea" Journal of Clinical Endocrinology and Metabolism 81(10):3615–21 (1996).

Visser, J.H. et al. "Luteinizing hormone, follicle–stimulating hormone, testosterone and dihydrotestosterone during testicular descent in the pig fetus" Reproduction, Fertility, and Development 8(7):1115–20 (1996).

Weiss, D.B. et al. "Follicle–stimulating hormone in azoospermia in prediction of spermatogenic patterns" Harefuah 135(5–6):169–75 (1998).

Weissman, A. et al. "Recovery of corpus luteum function after prolonged deprivation from gonadotrophin stimulation" Human Reproduction 11(5): 943–9 (1996).

Westhuizen, van der, S. et al. "Ovarian morphology as a predictor of hormonal values in polycystic ovary syndrome" Ultrasound in Obstetrics and Gynecology 7(5):335–41 (1996).

Feng–Y. et al., "Gonadotropins stimulate the proliferation of human epithelial ovarian cancer cell," Chinese Journal of Obstetrics and Gynecology 31(3):166–8 (1996).

Pinski et al., Inhibitory Effects of Analogs of Luteinizing Hormone–Releasing Hormone on the Growth of the Androgen–Independent Dunning R–3327–AT–1 Rat Prostate Cancer. Int. J. Cancer, 1994, vol. 59, pp. 51–55.

* cited by examiner

METHODS FOR TREATING FSH RELATED CONDITIONS WITH GNRH ANTAGONISTS

RELATED APPLICATIONS

This application claims priority to U.S. Provisional Application No. 60/185,573, filed on Feb. 28, 2000; U.S. Provisional Application No. 60/185,574, filed on Feb. 28, 2000; U.S. Provisional Application No. 60/238,337, filed on Oct. 5, 2000; and U.S. Provisional Application No. 60/238,338, filed on Oct. 5, 2000, each of which is incorporated herein in its entirety by this reference.

BACKGROUND OF THE INVENTION

Luteinizing hormone (LH) and follicle-stimulating hormone (FSH) are hormones released by the pituitary gland. These hormones regulate the functioning of the gonads and the production and maturation of gametes. LH and FSH are generally released by the pituitary gland upon prior release of a triggering hormone from the hypothalamus. Luteinizing hormone-releasing hormone (LHRH; also known as gonadotropin-releasing hormone or GnRH) is one of the principal hypothalamic hormones that triggers the release of LH and FSH. Thus, release of GnRH represents a control point in the physiological regulation of gonadal function.

LH and FSH release is necessary for ovulation in females and for maturation of sperm in males. Accordingly, compounds which inhibit LH and/or FSH release by blocking the action of GnRH, such as GnRH superagonists and antagonists, are useful in the treatment of sex-hormone associated disorders.

To decrease LH production, superagonists of the gonadotropin releasing hormone receptor (GnRH-R), such as leuprolide and goserelin, have been used. However, such GnRH superagonists initially act to stimulate LH release (and, frequently, testosterone or estrogen production) and only after prolonged treatment act to desensitize GnRH-R such that LH is no longer produced. In prostate cancer patients, for example, the initial stimulation of LH production by the superagonist leads to an initial surge in the production of male hormones such that the initial response to superagonist therapy is aggravation, rather than amelioration, of the patient's condition (e.g., tumor growth increases). This phenomenon, known as the "flare reaction", can last for two to four weeks. Additionally, each successive administration of the superagonist can cause a small LH surge (known as the "acute-on chronic" phenomenon) that again can worsen the condition.

Antagonists of the gonadotropin releasing hormone receptor (GnRH-R) have been developed to overcome the flare reaction associated with GnRH agonists. A typical problem, however, that is frequently encountered with GnRH antagonist peptides is the occurrence of histamine-releasing activity. This histamine-releasing activity represents a serious obstacle to the clinical use of such antagonists because histamine release results in adverse side effects such as edema and itching. Many GnRH antagonist peptides also suffer from poor water-solubility, which complicates formulation of the antagonist for administration in vivo. Due to these characteristics, only a subset of GnRH antagonists are suitable for in vivo use.

Even among GnRH antagonists that have been used in vivo, such as Cetrorelix and Nal-Glu, it has been reported that while these antagonists reduced LH levels, they did not significantly affect FSH levels when the antagonist was administered to the subject in a single bolus injection (Reissmann T, et al. *Human Reproduction* (1995) 10(8): 1974–81 and Diedrich K, et al. *Human Reproduction* (1994) 9(5):788–91).

Accordingly, GnRH antagonists that are suitable for use in vivo (e.g., they have high water solubility and low histamine-releasing activity) and that are able to inhibit LH and/or FSH production in a subject, are suitable for use in FSH related conditions, although prior attempts to reduce FSH levels with GnRH antagonists were inadequate.

SUMMARY OF THE INVENTION

The present invention provides GnRH antagonists, and formulations thereof, that are suitable for use in vivo and that are able to inhibit both LH and FSH production, and their use in treating FSH related conditions. The present invention is based, at least in part, on the discovery that treatment of subjects with GnRH antagonists, e.g., abarelix, using sustained release formulations such as those described herein, allows for the long term suppression of FSH levels in the subject (as compared to, for example, FSH levels achieved after treatment with an GnRH agonist). Accordingly, the present invention provides a method for treating an FSH related condition, (e.g., prostatic intraepithelial neoplasia, vaginal bleeding, infertility, pedophilia, precocious puberty, prostate cancer, hormone refractory prostate cancer, ovarian cancer, benign prostatic hypertrophy, endometriosis, uterine fibroids, breast cancer, premenstrual syndrome, polycystic ovary syndrome, pituitary gonadotropin tumors, testicular cancer, ovarian cysts, disorders related to an LH/FSH ratio imbalance, or thyroid related disorders such as metabolic and weight disorders,) in a subject, preferably a human, with such antagonists. The method includes administering to the subject an GnRH antagonist suitable for in vivo administration and able to reduce both plasma FSH and LH levels in a subject, in an amount or in a formulation effective to reduce plasma FSH levels in the subject to a symptom alleviating level, thereby treating an FSH related condition in the subject. In one embodiment, the symptom alleviating level of FSH is 4 ng/dL or less, 3 ng/dL or less, 2 ng/dL or less or about 1 ng/dL. In a preferred embodiment, the symptom alleviating level is 5 mIU/ml or less, 4 mIU/ml or less, 3 mIU/ml or less, 2 mIU/ml or less, or 1 mIU/ml or less. Ranges intermediate to the above recited values, e.g., 1–4 mIU/ml, 1–3 mIU/ml, or 2–4 mIU/ml, are also intended to be part of this invention. For example, ranges using a combination of any of the above recited values as upper and/or lower limits are intended to be included.

In a preferred embodiment, the GnRH antagonist is a decapeptide or a nonapeptide compound having a D-asparagine, an L-asparagine, a D-glutamine, or an L-glutamine at a position corresponding to position 6 of naturally occurring GnRH, or a pharmaceutically acceptable salt thereof. In one embodiment, the GnRH antagonist is a peptide compound comprising a structure: A-B-C-D-E-F-G-H-I-J, wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Trp, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn or D-Gln; G is Leu or Trp, or an analogue thereof; H is Lys(iPr), Gln, Met, or Arg, or an analogue thereof; I is Pro, or an analogue thereof; and J is Gly-NH$_2$ or D-Ala-NH$_2$, or an analogue thereof; or a pharmaceutically acceptable salt thereof. In another embodiment, the GnRH antagonist is a peptide compound comprising a structure: A-B-C-D-E-F-G-H-I-J, wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Trp, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn; G is Leu or Trp, or an analogue thereof, H is Lys(iPr), Gln, Met, or Arg, or an analogue thereof; I is Pro, or an analogue thereof; and J is Gly-NH$_2$ or D-Ala-NH$_2$, or an analogue thereof; or a pharmaceutically acceptable salt thereof.

In preferred embodiments, the GnRH antagonist is a peptide compound comprising a structure: Ac-D-Nal-4-Cl-D-Phe-D-Pal-Ser-N-Me-Tyr-D-Asn-Leu-Lys(iPr)-Pro-D-Ala-NH$_2$ or Ac-D-Nal-4-Cl-D-Phe-D-Pal-Ser-Tyr-D-Asn-Leu-Lys(iPr)-Pro-D-Ala-NH$_2$ or a pharmaceutically acceptable salt thereof.

In another preferred embodiment, the GnRH antagonist has an ED$_{50}$ for histamine release in a standard in vitro histamine release assay of at least 3 µg/ml, 5 µg/ml, or 10 µg/ml. In one embodiment, the GnRH antagonist is administered to the subject using a pharmaceutical composition comprising a solid ionic complex of the GnRH antagonist and a carrier macromolecule, wherein the carrier and GnRH antagonist used to form the complex are combined at a weight ratio of carrier:GnRH antagonist of 0.8:1 to 0.1:1. In a preferred embodiment, the complex is not a microcapsule. Ranges intermediate to the above recited values, e.g., 0.8:1 to 0.4:1, 0.6:1 to 0.2:1, or 0.5:1 to 0.1:1 are also intended to be part of this invention. Other possible ratios of carrier:GnRH antagonist include 0.5:1, 0.4:1, 0.3:1, 0.25:1, 0.15:1, and 0.1:1. Moreover, ranges of values using a combination of any of the above recited values as upper and/or lower limits are intended to be included.

In another embodiment, the GnRH antagonist is administered to the subject using a pharmaceutical composition comprising a solid ionic complex of a GnRH antagonist and a carrier macromolecule, wherein the GnRH antagonist content of said complex is at least 40% by weight, preferably at least 45%, 50%, 55%, 57%, 60%, 65%, 70%, 75%, 80%, 85%, 90%, or 95% by weight. Ranges intermediate to the above recited values, e.g., at least about 50% to about 80%, at least about 60% to about 90%, or at least about 57% to about 80%, are also intended to be part of this invention. For example, ranges of values using a combination of any of the above recited values as upper and/or lower limits are intended to be included.

In another embodiment, the dosage of the GnRH antagonist is about 10–500 mg/month in a sustained-release form, about 20–300 mg/month in a sustained-release form, or about 30–200 mg/month in a sustained-release form. In a preferred embodiment, the dosage of the GnRH antagonist is about 30–120 mg/month in a sustained-release form. Ranges intermediate to the above recited values, e.g., about 10–200 mg/month in a sustained-release form, about 30–250 mg/month in a sustained-release form, or about 100–200 mg/month in a sustained-release form, are also intended to be part of this invention. For example, ranges of values using a combination of any of the above recited values as upper and/or lower limits are intended to be included. The above recited dosages may also be calculated and expressed in mg/kg/day (based on an average subject weight of about 73 kg). Accordingly, in another embodiment, the dosage of the GnRH antagonist is about 5–500 µg/kg/day, about 10–400 µg/kg/day, or about 20–200 µg/kg/day. In a preferred embodiment, the dosage of the GnRH antagonist is about 100 µg/kg/day.

In another aspect, the invention features a method for treating prostatic intraepithelial neoplasia in a male subject, preferably a human male. The method includes administering to the subject a GnRH antagonist suitable for in vivo administration and able to reduce both plasma FSH and LH levels in a male subject, in an amount or in a formulation effective to reduce plasma FSH levels in the male subject, e.g., to a symptom alleviating level, thereby treating prostatic intraepithelial neoplasia in the male subject.

In another aspect, the invention features a method for treating vaginal bleeding in a female subject, preferably, a human female. The method includes administering to the subject a GnRH antagonist suitable for in vivo administration and able to reduce both plasma FSH and LH levels in a female subject, in an amount or in a formulation effective to reduce plasma FSH levels in the female subject, e.g., to a symptom alleviating level, thereby treating vaginal bleeding in the female subject. In one embodiment, the vaginal bleeding is due to thrombocytopenia, for example, caused by chemotherapy treatment. In another embodiment, the female subject is suffering from a proliferative disorder, e.g., acute myeloid leukemia. In another embodiment, the female subject is a transplant recipient.

In yet another aspect, the invention features a method for contraception in a male subject, preferably a human male. The method includes administering to the subject an GnRH antagonist suitable for in vivo administration and able to reduce both plasma FSH and LH levels in a male subject, in an amount or in a formulation effective to reduce plasma FSH levels in the male subject, e.g., to a symptom alleviating level, and administering testosterone to the male subject in an amount or in a formulation effective to restore libido and potency in the male subject. In one embodiment, the testosterone is administered to the male subject after the GnRH antagonist is administered. In another embodiment, the testosterone is administered to the male subject before the GnRH antagonist is administered. In yet another embodiment, the testosterone is administered to the male subject simultaneously with the GnRH antagonist.

In yet another aspect, the invention features a method for modulating, e.g., downregulating or upregulating, libido in a subject, preferably, a human. The method includes administering to the subject a GnRH antagonist suitable for in vivo administration and able to reduce both plasma FSH and LH levels in a subject, in an amount or in a formulation effective to reduce plasma FSH levels in the subject, e.g., to a symptom alleviating level, thereby modulating libido in the subject. In one embodiment, the subject is characterized as a pedophile, e.g., a subject voluntarily seeking treatment for pedophilia or a subject seeking treatment for pedophilia due to a court order.

In another aspect, the invention features a method for treating infertility in a female subject. The method includes administering to the subject a GnRH antagonist suitable for in vivo administration and able to reduce both plasma FSH and LH levels in a female subject, in an amount or in a formulation effective to reduce plasma FSH levels in the female subject to a symptom alleviating level; harvesting an ovum from the female subject before the effect of the GnRH antagonist has dissipated; combining the ovum with a spermatozoon in vitro, thereby fertilizing the ovum; and transferring the fertilized ovum into the uterus of the female subject, thereby treating infertility in the female subject. Whether the effect of the GnRH antagonist has dissipated can be determined using one of the assays described herein, such as by examining whether FSH levels in the subject remain suppressed (indicative that the effect of the GnRH antagonist has not dissipated).

In a further aspect, the invention features a method for in vitro fertilization of an ovum. The method includes administering to a female subject a GnRH antagonist suitable for in vivo administration and able to reduce both plasma FSH and LH levels in a female subject, in an amount or in a formulation effective to reduce plasma FSH levels in the female subject to a symptom alleviating level; harvesting an ovum from the female subject before the effect of the GnRH antagonist has dissipated; and combining the ovum with a spermatozoon in vitro, to thereby fertilize the ovum. In a preferred embodiment, the method further includes transferring the fertilized ovum into a uterus of a female subject, e.g., the female subject from which the ovum was harvested or a different female subject.

In another aspect, the invention features a method for reducing FSH levels in a subject. The method involves administering to the subject a GnRH antagonist suitable for in vivo administration and able to reduce both plasma FSH and LH levels in a subject, in an amount or in a formulation effective to reduce plasma FSH levels in the subject, thereby reducing FSH levels in the subject.

Other features and advantages of the invention will be apparent from the following detailed description and claims.

DETAILED DESCRIPTION OF THE INVENTION

Figure 1:
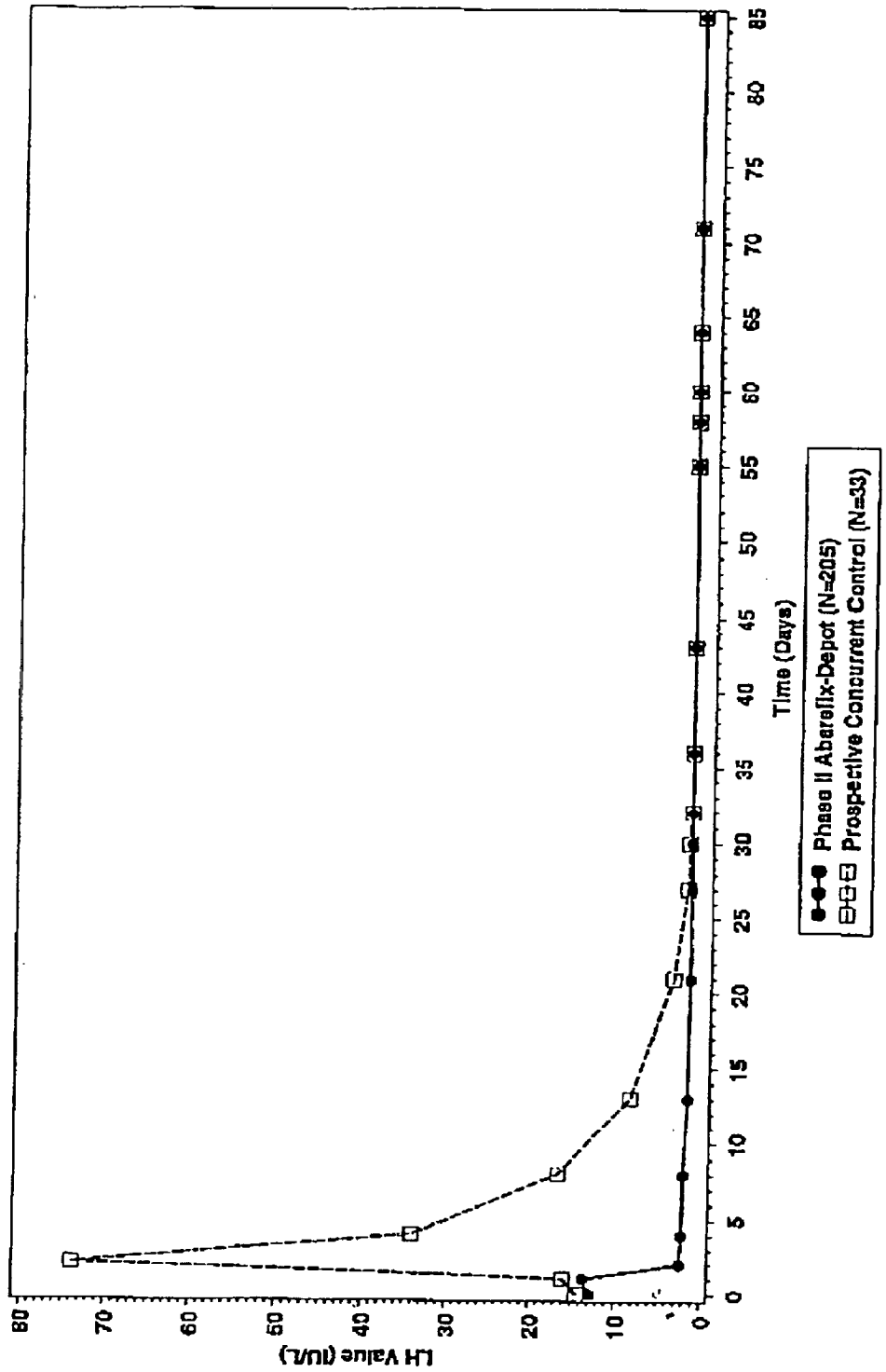
FIG. 1 is a graph depicting plasma LH levels in subjects participating in the Phase II clinical study described in Example 1.

The present invention provides GnRH antagonists, and formulations thereof, that are suitable for use in vivo and that inhibit both LH and FSH production, and their use in treating FSH related conditions. The present invention is based, at least in part, on the discovery that treatment of subjects with GnRH antagonists, e.g., abarelix, using sustained release formulations such as those described herein, allows for the long term suppression of FSH levels in the subject (as compared to, for example, FSH levels achieved after treatment with an GnRH agonist).

Accordingly, the present invention provides a method for treating an FSH related condition in a subject, preferably a human, with such antagonists. The method includes administering to the subject a GnRH antagonist suitable for in vivo administration and able to reduce both plasma FSH and LH levels in a subject, in an amount or in a formulation effective to reduce plasma FSH levels in the subject, e.g., to a symptom alleviating level, thereby treating an FSH related condition in the subject.

As used herein, the term "FSH related condition" includes any disease, disorder, or condition associated with the follicle stimulating hormone (FSH). FSH related conditions include conditions, diseases, or disorders which affect the organs of the reproductive system, e.g., the prostate gland, the uterus, or the vagina; conditions, diseases, or disorders which involve an imbalance in the levels of a reproductive-hormone in a subject; and conditions, diseases, or disorders affecting the ability of a subject to reproduce. FSH related conditions further include conditions, diseases, or disorders which affect the organs in which FSH receptors are expressed. Examples of FSH related conditions include prostatic intraepithelial neoplasia, vaginal bleeding, infertility, pedophilia, precocious puberty, prostate cancer, hormone-refractory prostate cancer, ovarian cancer, benign prostatic hypertrophy, endometriosis, uterine fibroids, breast cancer, premenstrual syndrome, polycystic ovary syndrome, pituitary gonadotropin tumors, testicular cancer, ovarian cysts, disorders related to an LH/FSH ratio imbalance, or thyroid related disorders such as metabolic and weight disorders, such as cachexia or obesity. In one embodiment, an FSH related condition is not intended to include precocious puberty, prostate cancer, ovarian cancer, benign prostatic hypertrophy, endometriosis, uterine fibroids, breast cancer, premenstrual syndrome, or polycystic ovary syndrome. As used herein, the term "hormone-refractory prostate cancer" is intended to include cancers of a type whose growth typically is promoted by sex hormones but whose ability to grow has become independent of sex hormones.

As used herein, the term "subject" includes warm-blooded animals, preferably mammals, including humans. In a preferred embodiment, the subject is a primate. In an even more preferred embodiment, the primate is a human.

As used herein, the term "GnRH antagonist" includes a compound that inhibits the gonadotropin releasing hormone receptor such that release of gonadotropins is inhibited. The term "GnRH antagonist" may be used interchangeably with the term "GnRH-R antagonist" to include compounds that inhibit GnRH-R such that release of both LH and FSH is inhibited. GnRH antagonists of the present invention are suitable for in vivo administration, e.g., they have good water solubility and/or low histamine-releasing activity. Preferred GnRH antagonists are those having low histamine-releasing activity (e.g., an $ED_{50}$ for histamine release in a standard in vitro histamine release assay of at least 3 µg/ml, more preferably at least 5 µg/ml, and still more preferably at least 10 µg/ml) and that exhibit water solubility. Histamine-releasing activity may be assayed by, for example, the method described in U.S. Pat. No. 4,851,385 to Roeske. Preferred GnRH antagonists with low histamine-releasing activity and water solubility include compounds disclosed in U.S. Pat. No. 5,843,901 issued Dec. 1, 1998, the entire contents of which are expressly incorporated herein by reference. An especially preferred GnRH antagonist comprises the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-GnRH (referred to herein as abarelix). The efficacy of candidate GnRH antagonists in inhibiting LH release can be assayed, for example, in an animal model such as that described in Corbin and Beattie, *Endocrine Res. Commun.* 2:1 (1975). In this assay, the GnRH antagonistic activity of a candidate compound is assayed by measuring the antiovulatory activity (AOA) of the compound in rats. The efficacy of candidate GnRH antagonists in inhibiting FSH release can be assayed, for example, using an assay described in Rose et al. *Endocrine Reviews* 21(1):5–22, the contents of which are incorporated herein by reference.

For reviews of GnRH antagonists, see also B. H. Vickery et al., eds., (1984) "GnRH and Its Analogs: Contraceptive and Therapeutic Applications", MTP Press Limited, Lancaster, Pa.; and G. Schaison (1989) *J. Steroid Biochem.* 33(4B): 795. Exemplary GnRH antagonists useful in the methods of the present invention include nona- and decapeptides, as well as peptidomimetics, that mimic the structure of natural GnRH. GnRH antagonists are described in further detail below.

As used herein, the term "administering" to a subject includes dispensing, delivering or applying an GnRH antagonist, e.g., an GnRH antagonist in a pharmaceutical formulation, to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the term "effective amount" includes an amount effective, at dosages and for periods of time necessary, to achieve the desired result, e.g., sufficient to treat an FSH related condition in a subject. An effective amount of an GnRH antagonist, as defined herein may vary according to factors such as the disease state, age, and weight of the subject, and the ability of the GnRH antagonist to elicit a desired response in the subject. Dosage regimens may be adjusted to provide the optimum therapeutic response. An effective amount is also one in which any toxic or detrimental effects (e.g., side effects) of the GnRH antagonist are outweighed by the therapeutically beneficial effects.

As used herein, the term "symptom alleviating level" refers to the plasma level of FSH in a subject that is sufficient to alleviate at least one symptom associated with an FSH related condition in the subject. For example, a symptom alleviating level of FSH in a subject can be less than about 5 ng/dL, preferably less than about 4 ng/dL, and more preferably less than about 3 ng/dL. A symptom alleviating level of FSH in a subject can be between about 5 ng/dL and 0 ng/dL. In a preferred embodiment, the symptom alleviating level is about 5 mIU/ml or less, about 4 mIU/ml or less, about 3 mIU/ml or less, about 2 mIU/ml or less, or about 1 mIU/ml or less. Ranges intermediate to the above recited values, e.g., about 1–4 mIU/ml, about 1–3 mIU/ml, or about 2–4 mIU/ml, are also intended to be part of this invention. For example, ranges using a combination of any of the above recited values as upper and/or lower limits are intended to be included.

As used herein, the term "FSH nadir" includes the point at which FSH levels, e.g, FSH plasma levels, in a subject do not decrease further even upon further treatment with an GnRH-R antagonist. For example, an FSH nadir has been reached in a subject when the plasma levels of FSH in a subject are less than 5 ng/dl, preferably less than 4 ng/dl, more preferably less than 3 ng/dl or less than 2 ng/dl, and even more preferably less than 1 ng/dl. Preferably, an FSH nadir has been reached in a subject when the plasma levels of FSH in a subject are less than 5 mIU/ml, preferably less than 4 mIU/ml, more preferably less than 3 mIU/ml or less than 2 mIU/ml, and even more preferably less than 1 mIU/ml.

In another aspect, the invention features a method for treating prostatic intraepithelial neoplasia in a male subject, preferably a human male. The method includes administering to the subject a GnRH antagonist suitable for in vivo administration and able to reduce both plasma FSH and LH levels in a male subject, in an amount or in a formulation effective to reduce plasma FSH levels in the male subject, e.g., to a symptom alleviating level, thereby treating prostatic intraepithelial neoplasia in the male subject.

As used herein, the term "prostatic intraepithelial neoplasia" or PIN includes the putative precancerous end of the morphologic continuum of cellular proliferation within prostatic ducts, ductules and acini. Two grades of PIN are identified, low grade and high grade. High grade PIN is considered to be a precursor to invasive carcinoma. The continuum which culminates in high grade PIN and early invasive cancer is characterized by basal cell layer disruption, basement membrane disruption, progressive loss of secretory differentiation markers, increasing nuclear and nucleolar abnormalities, increasing proliferative potential, and increasing variation in DNA content (aneuploidy). Clinical studies suggest that PIN precedes carcinoma by ten years or more, with low grade PIN first emerging in men in the third decade of life. Prostatic intraepithelial neoplasia is described in, for example, Colanzi P. et al. (1998) *Adv. Clin. Path.* 2(4):271–284 and Bostwick D. G. (1992) *J. Cell Biochem. Suppl.* 16H: 10–9, the contents of which are incorporated herein by reference.

In yet another aspect, the invention features a method for treating benign prostatic hypertrophy in a male subject, preferably a human male. The method includes administering to the subject a GnRH antagonist suitable for in vivo administration and able to reduce both plasma FSH and LH levels in a male subject, in an amount or in a formulation effective to reduce plasma FSH levels in the male subject, e.g., to a symptom alleviating level, thereby treating benign prostatic hypertrophy in the male subject.

As used herein, the term "benign prostatic hypertrophy" includes the non-malignant hypertrophy or enlargement of the prostate gland. Benign prostatic hypertrophy is described in, for example, Goonewardena S. A. (1998) *Ceylon Med. J.* 43(4):177–81 and Mebust W. K. (1992) *JAMA* 268(10) :1269, the contents of which are incorporated herein by reference.

In another aspect, the invention features a method for treating infertility in a female subject. The method includes administering to the subject an GnRH antagonist suitable for in vivo administration and able to reduce both plasma FSH and LH levels in a female subject, in an amount or in a formulation effective to reduce plasma FSH levels in the female subject to a symptom alleviating level; harvesting an ovum from the female subject before the effect of the GnRH antagonist has dissipated; combining the ovum with a spermatozoon in vitro, thereby fertilizing the ovum; and transferring the fertilized ovum into the uterus of the female subject, thereby treating infertility in the female subject. Whether the effect of the GnRH antagonist has dissipated may be determined using any of the assays described herein, for example by assessing plasma levels of FSH.

As used herein, the term "infertility" includes the inability to fertilize the ovum.

In a further aspect, the invention features a method for in vitro fertilization of an ovum. The method includes administering to a female subject a GnRH antagonist suitable for in vivo administration and able to reduce both plasma FSH and LH levels in a female subject, in an amount or in a formulation effective to reduce plasma FSH levels in the female subject to a symptom alleviating level; harvesting an ovum from the female subject before the effect of the GnRH antagonist has dissipated; and combining the ovum with a spermatozoon in vitro, to thereby fertilize the ovum. In a preferred embodiment, the method further includes transferring the fertilized ovum into a uterus of a female subject, e.g., the female subject from which the ovum was harvested or a different female subject. In various embodiments, the ovum is harvested from the female subject at about 1–30 days after GnRH antagonist administration, or alternatively, 1–21 days, 1–14 days, or 1–7 days after GnRH antagonist administration.

As used herein, the term "fertilization" includes a sequence of events that begin with contact between a spermatozoon and an ovum and end with the fusion of the nuclei of the spermatozoon and the ovum and the intermingling of maternal and paternal chromosomes. The term fertilization includes the passage of the spermatozoon through the corona radiata, the penetration of the zona pellucida by the sperm, the fusion of the ovum and spermatozoon cell membranes, and the fusion of the nuclei.

In yet another aspect, the invention features a method for contraception in a male subject, preferably a human male. The method includes administering to the subject a GnRH antagonist suitable for in vivo administration and able to reduce both plasma FSH and LH levels in a male subject, in an amount or in a formulation effective to reduce plasma FSH levels in the male subject, e.g., to a symptom alleviating level, and administering testosterone to the male subject in an amount or in a formulation effective to restore libido and potency in the male subject. Administration of testosterone can occur before, during and/or after administration of the GnRH antagonist.

As used herein, the term "contraception" includes the prevention of fertilization by chemical means, without destroying fertility of a subject.

As used herein, the term "libido" includes the sexual drive of a subject, for example, the conscious or unconscious sexual drive of a subject.

As used herein, the term "potency" includes the ability or capacity of a male subject to achieve an erection, i.e., the enlargement and stiffening of the penis.

In another aspect, the invention features a method for treating vaginal bleeding in a female subject, preferably, a human female. The method includes administering to the subject a GnRH antagonist suitable for in vivo administration and able to reduce both plasma FSH and LH levels in a female subject, in an amount or in a formulation effective to reduce plasma FSH levels in the female subject, e.g., to a symptom alleviating level, thereby treating vaginal bleeding in the female subject.

As used herein, the term "vaginal bleeding" includes bleeding through the vagina of a female subject, other than the normal monthly menstruation based on the menstrual cycle. The term vaginal bleeding includes bleeding of excessive duration or excessive amount; frequent menstruation; intermenstrual bleeding; and postmenopausal bleeding.

In one embodiment, the vaginal bleeding is due to thrombocytopenia, for example, caused by chemotherapy treatment. In another embodiment, the female subject is suffering from a proliferative disorder, e.g., acute myeloid leukemia. In another embodiment, the female subject is a transplant recipient.

As used herein, the term "thrombocytopenia" includes a condition in which the number of blood platelets is decreased, typically resulting in a tendency to bleed from capillaries.

In yet another aspect, the invention features a method for modulating, e.g., downregulating or upregulating, libido in a subject, preferably, a human. The method includes administering to the subject a GnRH antagonist suitable for in vivo administration and able to reduce both plasma FSH and LH levels in a subject, in amount effective to reduce plasma FSH levels in the subject, e.g., to a symptom alleviating level, thereby modulating libido in the subject. In one embodiment, the subject is characterized as a pedophile, e.g., a subject voluntarily seeking treatment for pedophilia or a subject seeking treatment for pedophilia due to a court order.

As used herein, the term "pedophile" includes a subject suffering from pedophilia, a sexual perversion in which children are the preferred sexual object.

In another aspect, the invention features a method for reducing FSH levels in a subject. The method includes administering to the subject aGnRH antagonist suitable for in vivo administration and able to reduce both plasma FSH and LH levels in a subject, in an amount or in a formulation effective to reduce plasma FSH levels in the subject, thereby reducing FSH levels in the subject.

Various aspects of the invention are described further in the following subsections.

GnRH Antagonists

GnRH antagonists preferred for use in the methods of the invention include those described in U.S. Pat. No. 5,843,901, the contents of which are incorporated herein by reference. For example, GnRH antagonists suitable for use in the methods of the invention include peptides comprising a structure:

A-B-C-D-E-F-G-H-I-J, wherein A is D-Glu, L-Glu, or an analogue thereof; B is D-His, L-His, or an analogue thereof; C is D-Trp, L-Trp, or an analogue thereof; D is D-Ser, L-Ser, or an analogue thereof; E is D-Tyr, L-Tyr, or an analogue thereof; F is D-asparagine, L-asparagine, D-glutamine, or L-glutamine; G is D-Leu, L-Leu or an analogue thereof; H is D-Arg, L-Arg, or an analogue thereof; I is D-Pro, L-Pro, or an analogue thereof; and J is D-Gly, L-Gly, or an analogue thereof; or a pharmaceutically acceptable salt thereof.

In a preferred embodiment, GnRH antagonists suitable for use in the methods of the invention include peptides comprising a structure:

A-B-C-D-E-F-G-H-I, wherein A is D-Glu, L-Glu, or an analogue thereof; B is D-His, L-His, or an analogue thereof; C is D-Trp, L-Trp, or an analogue thereof; D is D-Ser, L-Ser, or an analogue thereof; E is D-Tyr, L-Tyr, or an analogue thereof; F is D-asparagine, L-asparagine, D-glutamine, or L-glutamine; G is D-Leu, L-Leu or an analogue thereof; H is D-Arg, L-Arg, or an analogue thereof; and I is D-Pro, L-Pro, or an analogue thereof; or a pharmaceutically acceptable salt thereof.

In another embodiment, GnRH antagonists suitable for use in the methods of the invention include peptides comprising a structure:

A-B-C-D-E-F-G-H-I-J wherein A is pyro-Glu, Ac-Nal, Ac-Qal, Ac-Sar, or Ac-Pal, or an analogue thereof; B is His or 4-Cl-Phe, or an analogue thereof; C is Trp, Pal, Nal, Nal-Pal(N—O), or Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is Asn or Gln; G is Leu or Trp, or an analogue thereof; H is Lys(iPr), Gln, Met, or Arg, or an analogue thereof; I is Pro, or an analogue thereof; and J is Gly-NH₂ or Ala-NH₂, or an analogue thereof; or a pharmaceutically acceptable salt thereof.

In a preferred embodiment, GnRH antagonists suitable for use in the methods of the invention include peptides comprising a structure:

A-B-C-D-E-F-G-H-I-J wherein A is pyro-Glu, Ac-Nal, Ac-Qal, Ac-Sar, or Ac-Pal, or an analogue thereof; B is His or 4-Cl-Phe, or an analogue thereof; C is Trp, Pal, Nal, L-Nal-Pal(N—O), or Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is Asn; G is Leu or Trp, or an analogue thereof; H is Lys(iPr), Gln, Met, or Arg, or an analogue thereof; I is Pro, or an analogue thereof; and J is Gly-NH₂ or Ala-NH₂, or an analogue thereof; or a pharmaceutically acceptable salt thereof.

In one embodiment, GnRH antagonists suitable for use in the methods of the invention include peptides comprising a structure:

A-B-C-D-E-F-G-H-I wherein A is pyro-Glu, Ac-Nal, Ac-Qal, Ac-Sar, or Ac-Pal, or an analogue thereof; B is His or 4-Cl-Phe, or an analogue thereof; C is Trp, Pal, Nal, Nal-Pal(N—O), or Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is Asn or Gln; G is Leu or Trp, or an analogue thereof; H is Lys(iPr), Gln, Met, or Arg, or an analogue thereof; and I is Pro, or an analogue thereof; or a pharmaceutically acceptable salt thereof.

In a preferred embodiment, GnRH antagonists suitable for use in the methods of the invention include peptides comprising a structure:

A-B-C-D-E-F-G-H-I wherein A is pyro-Glu, Ac-Nal, Ac-Qal, Ac-Sar, or Ac-Pal, or an analogue thereof; B is His or 4-Cl-Phe, or an analogue thereof; C is Trp, Pal, Nal, L-Nal-Pal(N—O), or Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is Asn; G is Leu or Trp, or an analogue thereof; H is Lys(iPr), Gln, Met, or Arg, or an analogue thereof; and I is Pro, or an analogue thereof; or a pharmaceutically acceptable salt thereof.

In another embodiment, GnRH antagonists suitable for use in the methods of the invention include peptides comprising a structure:

A-B-C-D-E-F-G-H-I-J wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Trp, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn or D-Gln; G is Leu or Trp, or an analogue thereof; H is Lys(iPr), Gln, Met, or Arg, or an analogue thereof; I is Pro, or an analogue thereof; and J is Gly-NH₂ or D-Ala-NH₂, or an analogue thereof; or a pharmaceutically acceptable salt thereof.

In a preferred embodiment, GnRH antagonists suitable for use in the methods of the invention include peptides comprising a structure:

A-B-C-D-E-F-G-H-I-J wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Trp, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn; G is Leu or Trp, or an analogue thereof; H is Lys(iPr), Gln, Met, or Arg, or an analogue thereof; I is Pro, or an analogue thereof; and J is Gly-NH₂ or D-Ala-NH₂, or an analogue thereof; or a pharmaceutically acceptable salt thereof.

In another embodiment, GnRH antagonists suitable for use in the methods of the invention include peptides comprising a structure:

A-B-C-D-E-F-G-H-I wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Tip, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn or D-Gln; G is Leu or Trp, or an analogue thereof; H is Lys(iPr), Gln, Met, or Arg, or an analogue thereof; and I is Pro, or an analogue thereof; or a pharmaceutically acceptable salt thereof.

In a preferred embodiment, GnRH antagonists suitable for use in the methods of the invention include peptides comprising a structure:

A-B-C-D-E-F-G-H-I wherein A is pyro-Glu, Ac-D-Nal, Ac-D-Qal, Ac-Sar, or Ac-D-Pal, or an analogue thereof; B is His or 4-Cl-D-Phe, or an analogue thereof; C is Trp, D-Pal, D-Nal, L-Nal-D-Pal(N—O), or D-Trp, or an analogue thereof; D is Ser, or an analogue thereof; E is N-Me-Ala, Tyr, N-Me-Tyr, Ser, Lys(iPr), 4-Cl-Phe, His, Asn, Met, Ala, Arg or Ile, or an analogue thereof; F is D-Asn; G is Leu or Trp, or an analogue thereof; H is Lys(iPr), Gln, Met, or Arg, or an analogue thereof; and I is Pro, or an analogue thereof; or a pharmaceutically acceptable salt thereof.

In another embodiment, GnRH antagonists suitable for use in the methods of the invention include peptides comprising a structure:

B-C-D-E-F-G-H-I-J,

Wherein B is D-His, L-His, or an analogue thereof; C is D-Trp, L-Trp, or an analogue thereof; D is D-Ser, L-Ser, or an analogue thereof; E is D-Tyr, L-Tyr, or an analogue thereof; F is D-asparagine, L-asparagine, D-glutamine, or L-glutamine; G is D-Leu, L-Leu or an analogue thereof; H is D-Arg, L-Arg, or an analogue thereof; I is D-Pro, L-Pro, or an analogue thereof; and J is D-Gly, L-Gly, or an analogue thereof; or a pharmaceutically acceptable salt thereof.

In a preferred embodiment, GnRH antagonists suitable for use in the methods of the invention include peptides comprising a structure in which the amino acid corresponding to position 6 of the naturally occurring GnRH is D-asparagine or D-glutamine.

In another preferred embodiment, GnRH antagonists suitable for use in the methods of the invention include GnRH antagonists which inhibit ovulation in at least 50% of treated rats in a standard rat antiovulatory assay at a dose of 5 µg/rat and which have a low histamine-releasing activity. The term "histamine-releasing activity", as used herein, refers to the tendency of a compound to release histamine when administered to a subject. The histamine-releasing activity of a compound can be measured with an in vitro assay (described in more detail, infra). Preferred GnRH antagonist peptides have high activity in the rat antiovulatory activity assay, but low histamine releasing activity. Preferred GnRH antagonist peptides have an $ED_{50}$ in the histamine release assay of at least 3 µg/ml, more preferably at least 5 µg/ml, and still more preferably at least 10 µg/ml.

The GnRH antagonist peptides of the present invention also include peptide analogues. The term "peptide analogue" as used herein is intended to include molecules that mimic the chemical structure of a peptide and retain the functional properties of the peptide. A "residue" includes an amino acid or amino acid analogue incorporated in the peptide compound by an amide bond or amide bond mimetic. The term "amino acid analogue" includes molecules that mimic the chemical structure of naturally-occurring amino acids and that retain the functional properties of naturally-occurring amino acids includes a moiety, other than a naturally occurring amino acid, that conformationally and functionally serves as a substitute for a particular amino acid in a peptide compound without adversely interfering to a significant extent with the function of the peptide (e.g., interaction of the peptide with an GnRH receptor). In some circumstances, substitution with an amino acid analogue may actually enhance properties of the peptide (e.g., interaction of the peptide with an GnRH receptor). Examples of amino acid analogues include D-amino acids. GnRH antagonist peptides substituted with one or more D-amino acids may be made using well known peptide synthesis procedures.

Approaches for designing peptide analogs are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270.

Preferred GnRH antagonist peptides suitable for use in the methods of the present invention range in length from about 6 to 15 residues, preferably, from 8 to about 12 residues, more preferably from 9 to 11 residues, and most preferably are 10 residues in length.

The GnRH antagonist peptides of the present invention can be prepared by any suitable method for peptide synthesis, including solution-phase and solid-phase chemical synthesis. Preferably, the peptides are synthesized on a solid support. Methods for chemically synthesizing peptides are well known in the art (see, e.g., Bodansky, M. *Principles of Peptide Synthesis,* Springer Verlag, Berlin (1993) and Grant, G. A (ed.). *Synthetic Peptides: A User's Guide,* W. H. Freeman and Company, New York (1992). Automated peptide synthesizers useful to make the peptides of this invention are commercially available.

The use of combinatorial libraries to identify ligands is now well established (see, e.g., M. A. Gallop et al., (1994) *J. Med. Chem.* 37:1233; and E. M. Gordon et al., (1994) *J. Med. Chem.* 37:1385; and references cited therein). Therefore, additional GnRH antagonist peptides can be identified by chemical (e.g., solution or solid-phase) synthesis of combinatorial libraries (e.g., of peptides) and screening of the resulting libraries according to known techniques. Thus, many potential ligands can be synthesized and screened in a short period of time, and the most active ligands selected for further testing or use. Using the aforementioned techniques, GnRH antagonists suitable for use in the methods of the present invention may be identified.

As used herein, a GnRH antagonist further includes GnRH antagonists that have been described in the art such as cetrorelix and Nal-Glu; including antagonists described in e.g., U.S. Pat. No. 5,470,947 to Folkers et al.; Folkers et al., PCT Publication No. WO 89/01944; U.S. Pat. No. 5,413,990 to Haviv; U.S. Pat. No. 5,300,492 to Haviv; U.S. Pat. No. 5,371,070 to Koerber et al., U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al.

Pharmaceutical Compositions

GnRH antagonists suitable for use in the methods of the invention can be incorporated into pharmaceutical compositions suitable for administration to a subject, such as those described in U.S. Pat. No. 5,968,895, the contents of which are incorporated herein by reference, which allow for sustained delivery of the antagonists for a period of at least several weeks to a month or more. Preferably, a GnRH antagonist is the sole active ingredient formulated into the pharmaceutical composition, although in certain embodiments the GnRH antagonist may be combined with one or more other active ingredients such as a GnRH agonist, antiandrogen and/or inhibitor of sex steroid biosynthesis. In a preferred embodiment, the pharmaceutical composition comprises a GnRH antagonist and a pharmaceutically acceptable carrier.

Preferably, the GnRH antagonist is administered to the subject as a sustained-release formulation using a pharmaceutical composition comprising a solid ionic complex of an GnRH antagonist and a carrier macromolecule, wherein the carrier and GnRH antagonist used to form the complex are combined at a weight ratio of carrier:GnRH antagonist of for example, 0.5:1 to 0.1:1. In other embodiments, the carrier and GnRH antagonist used to form the complex are combined at a weight ratio of carrier:GnRH antagonist of 0.8:1, 0.7:1, 0.6:1, 0.5:1, 0.4:1, 0.3:1, 0.25:1, 0.2:1, 0.15:1, or 0.1:1. In a preferred embodiment, the complex is not a microcapsule. Ranges intermediate to the above recited values, e.g., 0.8:1 to 0.4:1, 0.6:1 to 0.2:1, or 0.5:1 to 0.1:1 are also intended to be part of this invention. For example, ranges of values using a combination of any of the above recited values as upper and/or lower limits are intended to be included.

In another embodiment, the GnRH antagonist is administered to the subject using a pharmaceutical composition comprising a solid ionic complex of an GnRH antagonist and a carrier macromolecule, wherein the GnRH antagonist content of said complex is at least 40% by weight, preferably at least 45%, 50%, 55%, 57%, 60%, 65%, 70%, 75%, 80%, 85%, 90%, or 95% by weight. Ranges intermediate to the above recited values, e.g., at least about 50% to about 80%, at least about 60% to about 90%, or at least about 57% to about 80%, are also intended to be part of this invention. For example, ranges of values using a combination of any of the above recited values as upper and/or lower limits are intended to be included.

As used herein, the term "carrier macromolecule" is intended to refer to a macromolecule that can complex with a peptide to form a water-insoluble complex. Preferably, the macromolecule has a molecular weight of at least 5 kDa, more preferably at least 10 kDa. The term "anionic carrier macromolecule" is intended to include negatively charged high molecular weight molecules, such as anionic polymers. The term "cationic carrier macromolecule" is intended to include positively charged high molecular weight molecules, such as cationic polymers.

As used herein, the term "water-insoluble complex" is intended to refer to a physically and chemically stable complex that forms upon appropriate combining of an GnRH antagonist and carrier macromolecule according to procedures described herein. This complex typically takes the form of a precipitate that is produced upon combining aqueous preparations of the GnRH antagonist and carrier macromolecule. Although not intending to be limited by mechanism, the formation of preferred water-insoluble complexes used in the methods of the invention is thought to involve (e.g., be mediated at least in part by) ionic interactions in situations where the GnRH antagonist is cationic and the carrier molecule is anionic or vice versa. Additionally or alternatively, the formation of a water-insoluble complex of the invention may involve (e.g., be mediated at least in part by) hydrophobic interactions. Still further, formation of a water-insoluble complex of the invention may involve (e.g., be mediated at least in part by) covalent interactions. Description of the complex as being "water-insoluble" is intended to indicate that the complex does not substantially or readily dissolve in water, as indicated by its precipitation from aqueous solution. However, it should be understood that a "water-insoluble" complex of the invention may exhibit limited solubility in water either in vitro or in the aqueous physiological environment in vivo.

As used herein, the term "sustained delivery" or "sustained release" is intended to refer to continual delivery of a GnRH antagonist in vivo over a period of time following administration, preferably at least several days, a week or several weeks and up to a month or more. In a preferred embodiment, a formulation of the invention achieves sustained delivery for at least about 28 days, at which point the sustained release formulation can be readministered to achieve sustained delivery for another 28 day period (which readministration can be repeated every 28 days to achieve sustained delivery for several months to years). Sustained delivery of the GnRH antagonist can be demonstrated by, for example, the continued therapeutic effect of the GnRH antagonist over time (e.g., by continued suppression of FSH and LH production over time). Alternatively, sustained delivery of the GnRH antagonist may be demonstrated by detecting the presence of the GnRH antagonist in vivo over time.

The complex used in the methods of the invention is prepared by combining the GnRH antagonist and the carrier macromolecule under conditions such that a water-insoluble complex of the GnRH antagonist and the carrier macromolecule forms.

For example, a solution of the GnRH antagonist and a solution of the carrier macromolecule are combined until a water-insoluble complex of the GnRH antagonist and the carrier macromolecule precipitates out of solution. In certain embodiments, the solutions of the GnRH antagonist and the carrier macromolecule are aqueous solutions. Alternatively, if the GnRH antagonist or the carrier molecule (or both) is not substantially water soluble prior to combination the two, then the GnRH antagonist and/or carrier macromolecule can be dissolved in a water-miscible solvent, such as an alcohol (e.g., ethanol) prior to combining the two components of the complex. In another embodiment of the method of preparing the water-insoluble complex, the solution of the GnRH antagonist and the solution of the carrier macromolecule are combined and heated until a water-insoluble complex of the GnRH antagonist and the carrier macromolecule precipitates out of solution. The amounts of GnRH antagonist and carrier macromolecule necessary to achieve the water-insoluble complex may vary depending upon the particular GnRH antagonist and carrier macromolecule used, the particular solvent(s) used and/or the procedure used to achieve the complex. Typically, however, the GnRH antagonist will be in excess relative to the anionic molecule on a molar basis. Often, the GnRH antagonist also will be in excess on a weight/weight basis, as indicated above. In certain embodiments, the carrier macromolecule is preferably carboxymethylcellulose, and the GnRH antagonist is preferably abarelix.

Once the GnRH antagonist/macromolecule complex precipitates out of solution, the precipitate can be removed from the solution by means known in the art, such as filtration (e.g., through a 0.45 micron nylon membrane), centrifugation and the like. The recovered paste then can be dried (e.g., in vacuum or in a 70° C. oven) and the solid can be milled or pulverized to a powder by means known in the art (e.g., hammer or gore milling, or grinding in mortar and pestle). Alternatively, the paste can be frozen and lyophilized to dryness. The powder form of the complex can be dispersed in a carrier solution to form a liquid suspension or semi-solid dispersion suitable for injection. Accordingly, in various embodiments, a pharmaceutical formulation of the invention is a lyophilized solid, a liquid suspension or a semi-solid dispersion.

In another embodiment, the pharmaceutical formulation used in the methods of the invention is a sterile formulation. For example, following formation of the water-insoluble complex, the complex can be sterilized, preferably by gamma irradiation or electron beam sterilization. Alternatively, to prepare a sterile pharmaceutical formulation, the water-insoluble complex can be isolated using conventional sterile techniques (e.g., using sterile starting materials and carrying out the production process aseptically).

The pharmaceutical formulation can be administered to the subject by any route suitable for achieving the desired therapeutic result(s), although preferred routes of administration are parenteral routes, in particular intramuscular (i.m.) injection and subcutaneous/intradermal (s.c./i.d.) injection. Alternatively, the formulation can be administered to the subject orally. Other suitable parental routes include intravenous injection, buccal administration, transdermal delivery and administration by the rectal, vaginal, intranasal or respiratory tract route. It should be noted that when a formulation that provides sustained delivery for weeks to months by the i.m or s.c./i.d. route is administered by an alternative route, there may not be sustained delivery of the agent for an equivalent length of time due to clearance of the agent by other physiological mechanisms (i.e., the dosage form may be cleared from the site of delivery such that prolonged therapeutic effects are not observed for time periods as long as those observed with i.m or s.c./i.d. injection).

The pharmaceutical formulation contains a therapeutically effective amount of the GnRH antagonist. A "therapeutically effective amount" refers to an amount effective, at dosages and for periods of time necessary, to achieve the desired result. A therapeutically effective amount of an GnRH antagonist may vary according to factors such as the disease state, age, and weight of the individual, and the ability of the GnRH antagonist (alone or in combination with one or more other drugs) to elicit a desired response in the individual. Dosage regimens may be adjusted to provide the optimum therapeutic response. A therapeutically effective amount is also one in which any toxic or detrimental effects of the antagonist are outweighed by the therapeutically beneficial effects.

In one embodiment, the dosage of the LHRH antagonist is about 10–500 mg/month, about 20–300 mg/month, or about 30–200 mg/month. In a preferred embodiment, the dosage of the LHRH antagonist is about 30–120 mg/month. Ranges intermediate to the above recited values, e.g., about 10–200 mg/month, about 30–250 mg/month, or about 100–200 mg/month, are also intended to be part of this invention. For example, ranges of values using a combination of any of the above recited values as upper and/or lower limits are intended to be included. The above recited dosages may also be calculated and expressed in mg/kg/day. Accordingly, in another embodiment, the dosage of the LHRH antagonist is about 5–500 μg/kg/day, about 10–400 μg/kg/day, or about 20–200 μg/kg/day. In a preferred embodiment, the dosage of the LHRH antagonist is about 100 μg/kg/day. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Preferred pharmaceutical compositions for use in the methods of the invention are the Depot formulations described in the Examples and prepared as described in U.S. Pat. No. 5,968,895, the contents of which are incorporated herein by reference. These depot formulations provide sustained delivery of a GnRH antagonist (abarelix) for a period of at least four weeks.

In vitro Fertilization

In a further aspect, the invention features a method for in vitro fertilization of an ovum. The method includes administering to the subject a GnRH antagonist suitable for in vivo administration and able to reduce both plasma FSH and LH levels in a female subject, in an amount or in a formulation effective to reduce plasma FSH levels in the female subject to a symptom alleviating level; harvesting an ovum from the female subject before the effect of the GnRH antagonist has dissipated; and combining the ovum with a spermatozoon in vitro, to thereby fertilize the ovum. In a preferred embodiment, the method further includes transferring the fertilized ovum into a uterus of a female subject.

Methods for harvesting ova from a female subject, as well as methods for combining the ova with spermatozoaria, and methods of transferring the fertilized ova into a uterus of a female subject are known in the art and are described in, for example, U.S. Pat. Nos. 5,882,928 and 5,882,928, Spyropoulou I. et al. (1999) *Hum. Reprod.*14(1):76–9, Kastrop P. M. et al. (1999) *Hum. Reprod.* 14(1):65–9, Russell J. B. et al. (1999) *Curr. Opin. Obstet. Gynecol.* 11(3):289–96, Gorrill M. J. et al. (1999) *Am. J. Obstet. Gynecol.* 180(6 Pt 1): 1472–1474, the entire contents of each of which are incorporated herein by reference.

This invention is further illustrated by the following examples which should not be construed as limiting. The contents of all references, patents and published patent applications cited throughout this application, as well as the Figures, are hereby incorporated by reference.

EXAMPLES

Example 1

The following example describes the results of a multicenter, open-label Phase II study that enrolled 242 men (prospective concurrent control, N=33; abarelix depot, N=209). The groups were well matched for age, weight, height, race, body mass, stage of disease, and Gleason score (Table 4).

TABLE 4

Demographic Characteristics Of Study Population

|  | abarelix depot (N = 209) | Concurrent controls (N = 33) |
|---|---|---|
| Age (years) | | |
| Mean (SD) | 72 ± 8.6 | 73 ± 6.2 |
| Range | 49–93 | 59–84 |
| Weight (lbs) | | |
| Mean (SD) | 188 ± 36.2 | 185 ± 28.0 |
| Range | 104–315 | 135–256 |
| No. (%) nonwhite[a] | 51 (24) | 11 (33) |
| ECOG status (%) | | |
| 0 | 201 (96) | 33 (100) |
| 1 | 5 (2) | 0 |
| 2 | 3 (1) | 0 |
| Categories of disease (%) | | |
| Stage $D_1/D_2$[b] | 25 (12) | 6 (18) |
| Increasing PSA after definitive local therapy | 53 (25) | 8 (24) |
| Neoadjuvant/intermittent therapy | 131 (63) | 19 (58) |

[a]African American, Hispanic, Asian, others
[b]$D_1$ = evidence of pelvic lymph note metastases; $D_2$ = extrapelvic soft tissue or bone metastases The institutional review boards of all participating institutions approved the study protocol, and all men gave written informed consent before any study procedure was done. Abarelix depot (100 mg) (prepared as described in U.S. Pat. No. 5,968,895) was delivered by intramuscular injection on days 1 and 15 and, depending on testosterone concentrations, 50 or 100 mg every 28 days for the duration of the study. The LHRH superagonists (e.g., leuprolide (Lupron Depot®) 7.5 mg) with or without an antiandrogen, were administered using different depot formulations. All men had identical baseline screening tests and on-study laboratory and endocrinologic evaluations during the first 12 weeks. Serum concentrations of FSH and other hormones were measured at baseline and at specified timepoints for the first 85 days of the study. The median FSH concentration at baseline was similar in the study and control groups (15.0 and 16.8 IU/L, respectively).

Figure 2:
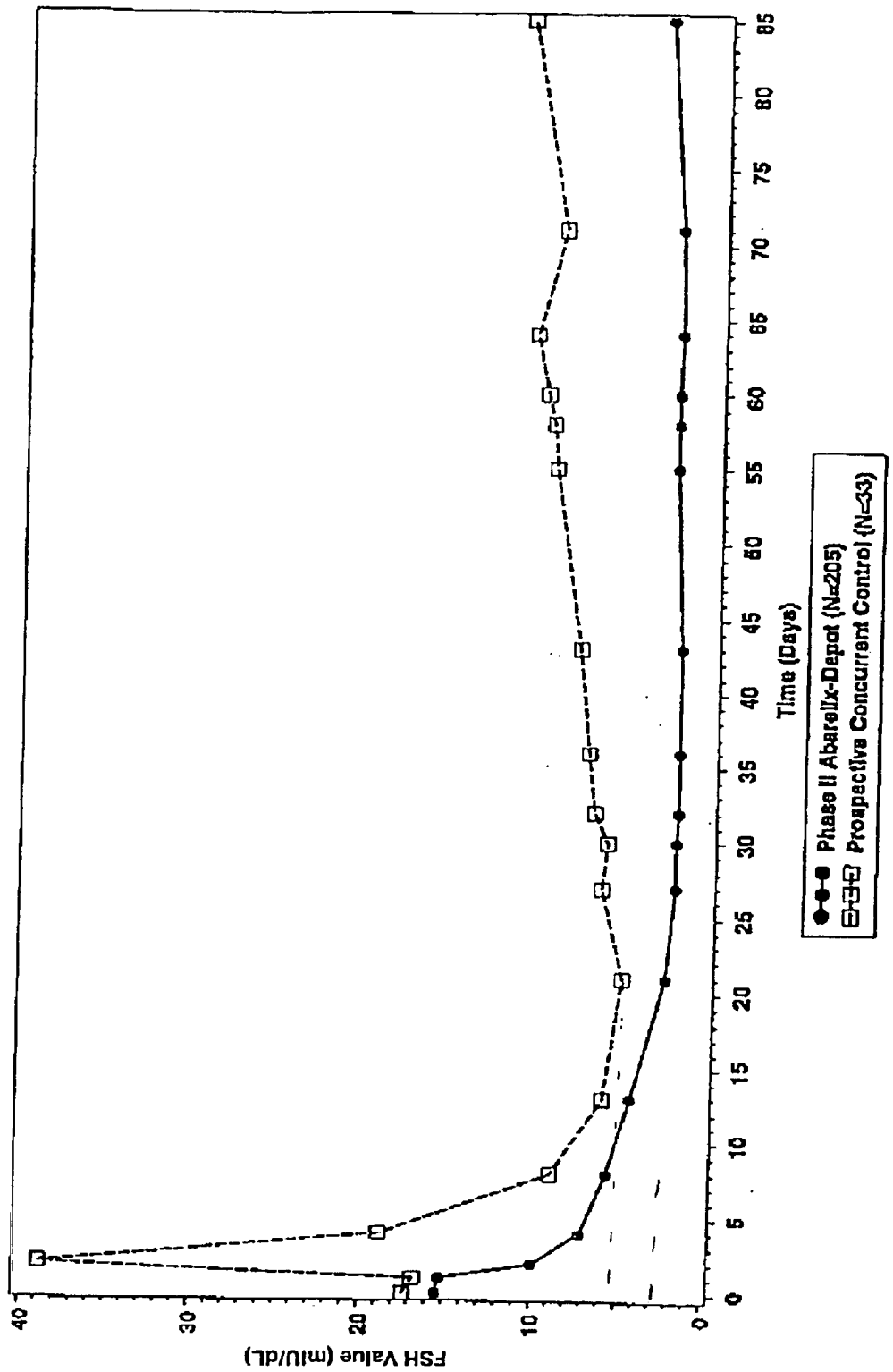
FIG. 2 is a graph depicting plasma FSH levels in subjects participating in the Phase II clinical study described in Example 1.

The median concentrations of FSH are shown in FIG. 2 and the median concentrations of LH are shown in FIG. 1. Men treated with LHRH superagonists, with or without antiandrogens, had a surge in the serum concentrations of FSH to a median of 38.8 IU/L on day 2 of the study, before the concentration decreased. The median concentration of serum FSH reached its lowest point (4.9 IU/L) on study day 21 before increasing to a median of 11.10 IU/L on day 85. Conversely, the men receiving abarelix depot had an immediate and sustained decrease in the serum concentration of FSH: the median concentration on day 2 was 10.0 IU/L. The serum concentration of FSH remained below 3.0 IU/L for all men in this group from day 21 to 85. The lowest concentrations (1.8 IU/L) were seen on days 32, 36, and 43.

These results demonstrate that LH levels decreased to comparable levels in the abarelix depot and the LHRH superagonist treated subjects (FIG. 1). However, FSH levels rose from nadir towards baseline in the LHRH superagonist treated subjects, whereas FSH levels remained at nadir in the abarelix depot treated subjects for a sustained period of time (FIG. 2).

Example 2

The following example describes results of experiments examining levels of FSH in plasma of human subjects treated with the GnRH antagonist abarelix, obtained from a Phase III clinical trial involving administration of abarelix to prostate cancer patients.

Study Design and Schema

The following Phase III clinical studies A and B (using the abarelix depot) were blinded, randomized, parallel-group, multicenter phase 3 trials conducted in adult male patients with prostate cancer who were candidates for initial hormonal therapy, including patients with local or regional disease who were candidates for neoadjuvant hormonal therapy; patients with metastatic disease (stage D1 or D2); patients with rising prostate specific antigen (PSA) levels after radical prostatectomy, radiation therapy, or other local therapy; and patients scheduled for their initial course of intermittent therapy.

Figure 3:
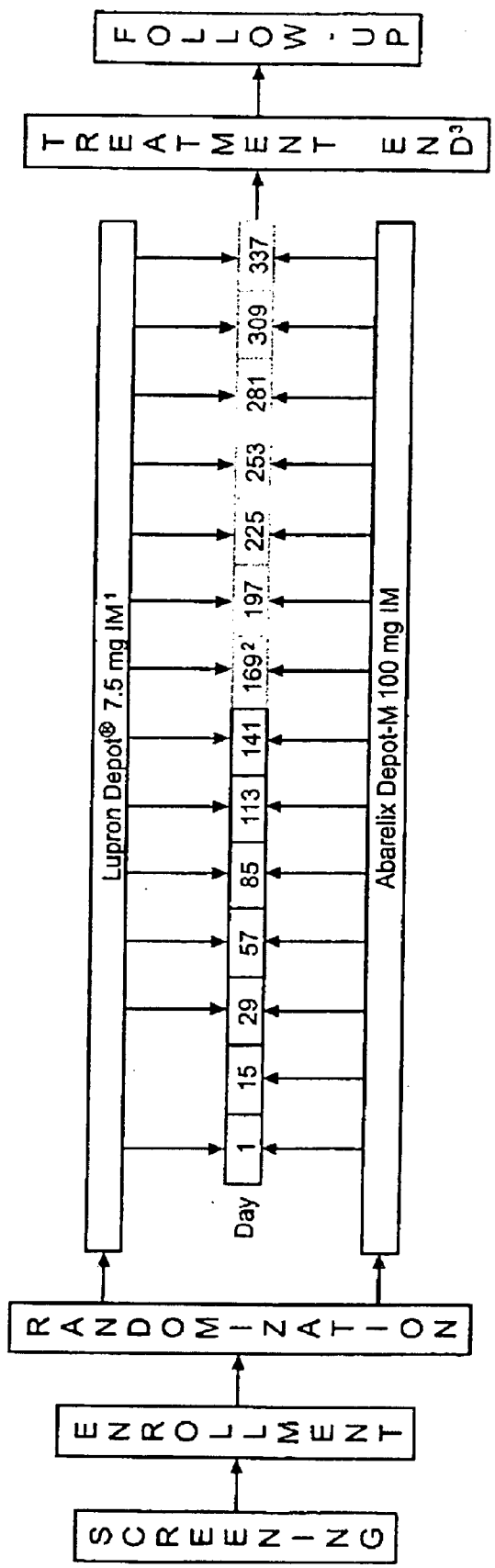
FIG. 3 is a graphic representation of the treatment schema for studies A and B, described in Example 1. In study A, leuprolide (Lupron Depot®) was given as monotherapy; in study B, it was given in combination with daily bicalutamide (Casodex®).

Patients were randomized to receive either abarelix depot 100 mg or active control medication (leuprolide (Lupron Depot®) 7.5 mg in study A; leuprolide (Lupron Depot®) 7.5 mg plus daily bicalutamide (Casodex®) in study B). As indicated in Table 1 (below) and FIG. 3, patients received abarelix depot or leuprolide (Lupron Depot®) by intramuscular (IM) injection on days 1, 29, 57, 85, 113, and 141. Patients in the abarelix depot group received an additional injection of study drug on day 15. As clinically indicated, patients could continue treatment with study drug for up to 1 year with injections on day 169 and every 28 days thereafter (up to 7 additional injections beyond day 141).

Depending on their day 169 testosterone levels (i.e., if >50 ng/dL), patients in the abarelix depot group received an extra injection of study drug on day 183 (2 weeks before their next regularly scheduled injection). Patients in the active control groups with testosterone >50 ng/dL on day 169 received a leuprolide (Lupron Depot®) 7.5 mg injection on day 169. These patients were then discontinued from active control medication and were dosed with abarelix depot beginning on day 197, 2 weeks later on day 211, 2 weeks after that on day 225, and every 28 days thereafter.

Results

In study A, 271 patients were enrolled, 91 patients were randomized to receive leuprolide (Lupron Depot®) 7.5 mg and 180 patients were randomized to receive abarelix depot. The first patient received study medication on 1, Dec. 1998, the last patient was first dose on 7, Apr. 1999, and the last patient completed the day 169 assessments on 14, Sep. 1999. Twenty-six centers in the United States enrolled at least 1 patient in the study.

In study B, 255 patients were enrolled, 85 patients were randomized to receive leuprolide (Lupron Depot®) plus bicalutamide (Casodex®) and 170 patients were randomized to receive abarelix depot. Twenty-two centers in the United States enrolled at least 1 patient in the study.

In study A, the median follicle-stimulating hormone (FSH) level in the active control group increased more than 2-fold over the baseline median on day 2 (see Table 2). By day 8 the median FSH level in the active control group was reduced to less than half of the baseline median (4.0 mIU/ml), and remained at approximately this level through day 85. In contrast, the median FSH level in the abarelix depot group decreased to well below baseline as early as day 2 (5.0 mIU/ml) and remained at this level through day 85.

TABLE 2

Study A: Median Serum Follicle-Stimulating Hormone Levels

| | Treatment Group | | | | |
| --- | --- | --- | --- | --- | --- |
| | Lupron Depot ® (leuprolide) N = 89 | | abarelix depot N = 180 | | |
| | n | Median FSH Levels (mIU/ml) | n | Median FSH Levels (mIU/ml) | p-value[1] |
| Baseline | 88 | 9.0 | 180 | 8.0 | 0.584 |
| Day 2 | 88 | 21.0 | 179 | 5.0 | <0.001 |
| Day 4 | 85 | 10.0 | 173 | 3.0 | <0.001 |

TABLE 1

Schedule of Events

| ASSESSMENTS | Screening/ Baseline Day-14 to Day 1 | Treatment (Study Days) | | | | | | | | 1.1 4 to 5 wks post last month of treatment (8–9 wks post last injection) |
| --- | --- | --- | --- | --- | --- | --- | --- | --- | --- | --- |
| | | 1 | 2 | 4 | 8 | 15 | | | | |
| | | 29 57 113 141 | 30 58 | 32 60 | 36 64 | | 43 | 71 | 99 127 155 | 85 169 |
| Informed Consent | X | | | | | | | | | |
| Special Chemistry Panel[1,2] | X | X | X | X | X | X | X | X | X | X |
| abarelix-depot[3] | | X | | | | X | | | | X |
| Lupron ® Depot 1-Month[3] (leuprolide) | | X | | | | | | | | X |
| daily Casodex ® (Study B)[3] bicalutamide | | X | X | X | X | X | X | X | X | |

[1]Special Chemistry Panel (includes FSH)
[2]Patients on study beyond Day 169 are to have FSH performed every 28 days. Also required 28 days post last injection, to conclude treatment portion of study.
[3]abarelix depot - Dose on Days 1, 15, 29, 57, 85, 113 and 141 - 100 mg IM. Leuprolide (Lupron ® Depot) 1-Month - Dose on Days 1, 29, 57, 85, 113 and 141 - 7.5 mg plus daily bicalutamide (Casodex ®). Day 1 through Day 169. If continuing on treatment see section V.C. Treatment for dosing beyond Day 169.

TABLE 2-continued

Study A: Median Serum Follicle-Stimulating Hormone Levels

| | Treatment Group | | | | |
|---|---|---|---|---|---|
| | Lupron Depot ® (leuprolide) N = 89 | | abarelix depot N = 180 | | |
| | n | Median FSH Levels (mIU/ml) | n | Median FSH Levels (mIU/ml) | p-value[1] |
| Day 8 | 82 | 4.0 | 177 | 3.0 | <0.001 |
| Day 15 | 88 | 2.5 | 179 | 2.0 | 0.842 |
| Day 29 | 88 | 3.0 | 179 | 1.0 | |
| Day 57 | 85 | 4.0 | 174 | 1.0 | |
| Day 85 | 86 | 4.5 | 175 | 2.0 | |

[1]Wilcoxon rank sum test

In study B, the median FSH level in the active control group increased more than 2-fold over the baseline median level at day 2, followed by a subsequent decrease to approximately half of the baseline level (see Table 3). In the abarelix depot group, the median FSH level decreased to well below the baseline median value by day 2, and subsequently steadily decreased to 1 mIU/ml (detection limit of the assay).

TABLE 3

Study B: Median Serum Follicle-Stimulating Hormone Levels

| | Treatment Group | | | | |
|---|---|---|---|---|---|
| | Lupron Depot ® (leuprolide) plus Casodex ® (bicalutamide) N = 83 | | abarelix depot N = 168 | | |
| | n | Median FSH Levels (mIU/ml) | n | Median FSH Levels (mIU/ml) | p-value[1] |
| Baseline | 83 | 8.0 | 167 | 8.0 | 0.853 |
| Day 2 | 80 | 17.0 | 165 | 5.0 | <0.001 |
| Day 4 | 80 | 8.5 | 162 | 4.0 | <0.001 |
| Day 8 | 79 | 4.0 | 165 | 3.0 | 0.014 |
| Day 15 | 79 | 3.0 | 165 | 2.0 | 0.363 |
| Day 29 | 81 | 3.0 | 168 | 1.0 | |
| Day 57 | 78 | 4.0 | 164 | 1.0 | |
| Day 85 | 80 | 5.0 | 164 | 1.0 | |

[1]Wilcoxon rank sum test

Figure 4A:
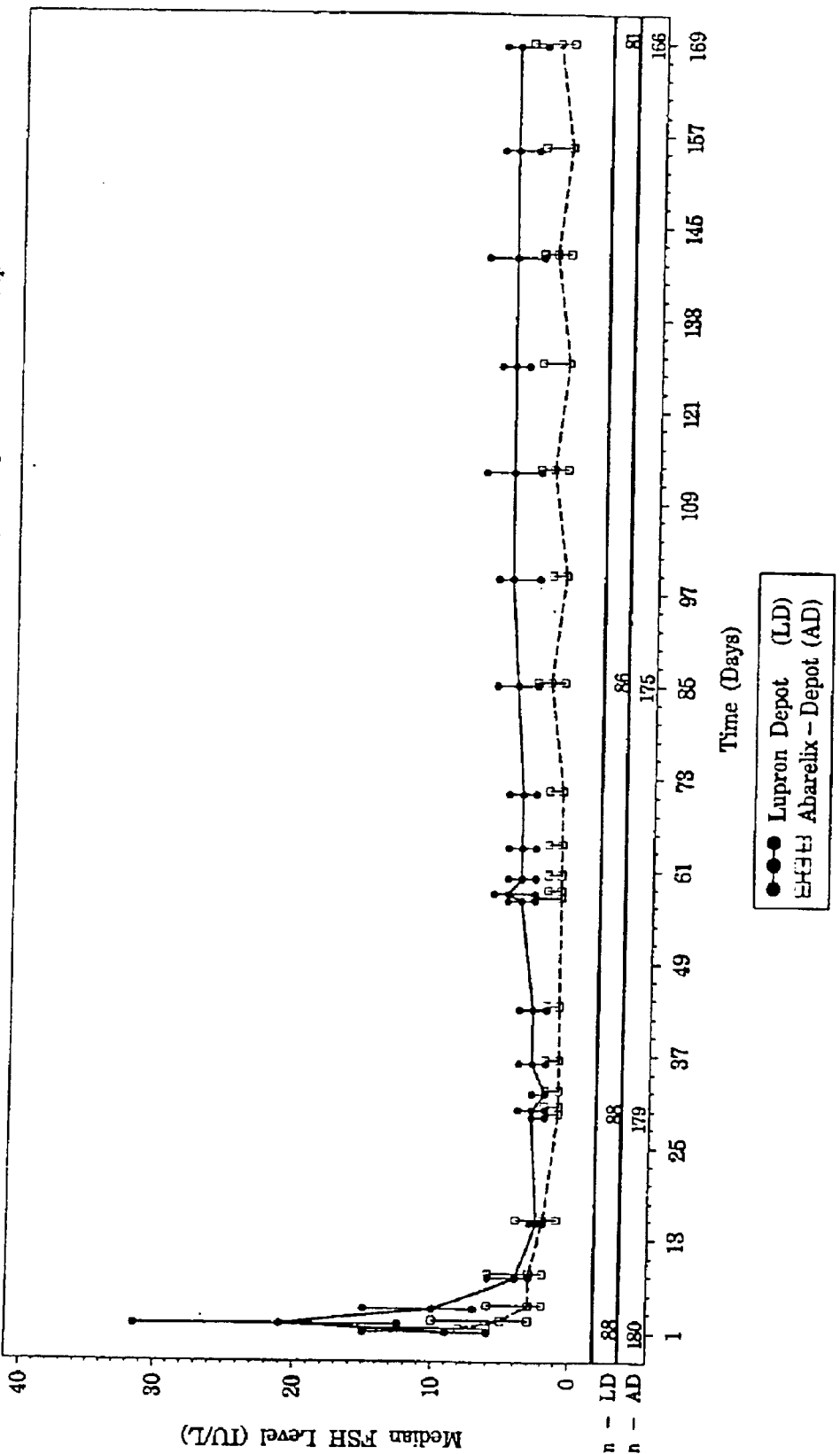
FIG. 4A is a graph depicting plasma FSH and LH levels in subjects participating in Phase III clinical study A, described in Example 2.
Figure 4B:
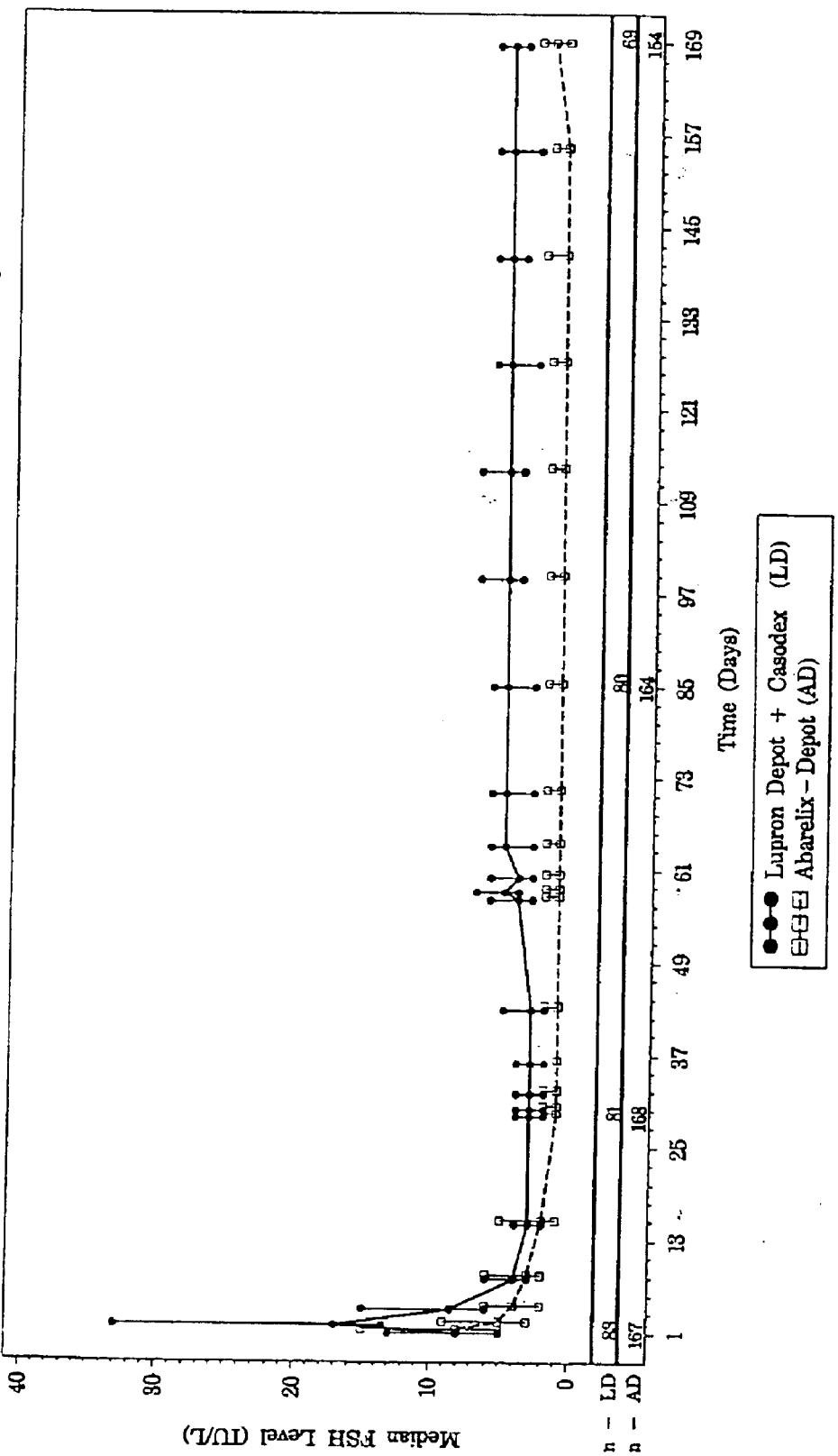
FIG. 4B is a graph depicting plasma FSH and LH levels in subjects participating in Phase III clinical study B, described in Example 2.

Thus, as indicated in Tables 2 and 3 and in FIG. 4, in both studies A and B, abarelix depot was superior to active control medication (i.e., leuprolide (Lupron Depot®)) in rapidly suppressing FSH levels. Median FSH levels were significantly lower in the abarelix depot group than in the active control group on day 2 through day 8. In addition, the suppression of FSH appeared to be more robust in abarelix depot group versus the active control group from day 29 through day 85.

Example 3

The effect of abarelix depot on FSH levels was further evaluated in phase III multicenter studies and compared to the effect of leuprolide±bicalutamide (L±B) on FSH levels. FSH levels were measured throughout the study in patients treated with injections of 100 mg abarelix depot and 7.5 mg leuprolide±oral daily bicalutamide 50 mg. Avoidance of FSH surge (50% over baseline FSH) on day 2 and maintenance of FSH suppression (≦FSH at baseline) on day 169 were evaluated in 512 patients. Data from the two studies was pooled for abarelix depot treated patients.

TABLE 5

Patients (%) with FSH Response

| | abarelix depot | leuprolide | leuprolide + bicalutamide |
|---|---|---|---|
| Avoidance of FSH surge | 345/345 (100%) | 14/87 (16%) | 8/80 (10%) |
| Maintenance of FSH Suppression (day 169) | 312/322 (97%) | 66/80 (82%) | 48/69 (70%) |

FSH levels were rapidly suppressed with abarelix depot as compared to L±B. None of the abarelix depot treated patients versus 84% of the leuprolide (Lupron Depot®) treated and 90% of the L+B treated patients experienced a hormone surge. FSH suppression was maintained in all but 3% of the abarelix depot treated patients as compared to 18% of the leuprolide (Lupron Depot®) treated and 30% of the L+B treated patients (see Table 5). The foregoing data indicates that in comparison with leuprolide with or without bicalutamide, abarelix depot demonstrates a different effect on FSH manifested as: a more rapid reduction in FSH levels, avoidance of FSH surge, and greater maintenance of FSH suppression.

Example 4

The effect of abarelix depot treatment on FSH levels was compared to the effect of L±B treatment on FSH levels in two large phase III trials in early and late stage PC patients who were candidates for initial hormonal therapy. Patients were randomized to receive monthly intramuscular injections of abarelix depot 100 mg or leuprolide 7.5 mg±daily oral bicalutamide 50 mg. Abarelix depot treated patients received an additional injection on day 15. FSH levels were measured at frequent intervals throughout the study. Avoidance of FSH surge (50% over baseline) on day 2 and maintenance of FSH suppression (≦FSH at baseline) on day 169 were evaluated in 512 patients. Abarelix depot data from the two studies were pooled. The results of this study are set forth in Table 6.

TABLE 6

FSH Levels (ng/mL)

| | Day 1 | Day 2 | Day 4 | Day 29 | Day 85 | Day 169 |
|---|---|---|---|---|---|---|
| leuprolide | 15 | 31.5 | 15 | 3 | 4.5 | 5 |
| leuprolide ± bicalutamide | 8 | 17 | 8.5 | 3 | 5 | 5 |
| abarelix depot | 8 | 5 | 4 | 1 | 1 | 2 |

FSH surge was avoided in 100% of abarelix depot treated patients as compared to 16% of leuprolide treated patients and 10% of L+B treated patients. All but 3% of patients treated with abarelix depot versus 18% and 30% of patients treated with leuprolide and L+B, respectively, maintained suppression of FSH at day 169. As indicated by these results, in comparison with leuprolide±bicalutamide, abarelix depot demonstrated a differential effect on FSH. Abarelix depot: 1) avoided the initial surge in FSH; 2) suppressed FSH faster and to a lower level; and 3) more effectively maintained suppression of FSH.

Example 5

The following example describes results of experiments examining levels of FSH in plasma of human female subjects treated with the GnRH antagonist abarelix, obtained from a clinical trial involving administration of abarelix to endometriosis patients.

Forty patients (randomized into five arms (4 abarelix depot doses, 1 leuprolide dose)) were randomized to receive one of four doses of abarelix depot (30, 60, 90, and 120 mg) administered subcutaneously every 4 weeks for 24 weeks or leuprolide (Lupron Depot®) 3.75 mg administered intramuscularly every 4 weeks for 24 weeks. The patients were evaluated for hormonal levels and the data obtained from this study are set forth in Table 7.

TABLE 7

| | FSH (mIU/mL) Median (min, max) | | | | |
|---|---|---|---|---|---|
| | Lupron | Abarelix 30 mg | Abarelix 60 mg | Abarelix 90 mg | Abarelix 120 mg |
| Day 1, 0 hr | 6.5 (5, 13) | 7 (5, 11) | 9 (5, 13) | 7 (6, 13) | 6 (4, 8) |
| Day 1, 2 hr | 16 (9, 27) | 6 (4, 9) | 8 (4, 12) | 6 (5, 12) | 5 (3, 7) |
| Day 1, 4 hr | 28 (13, 47) | 6 (4, 8) | 6 (3, 11) | 6 (5, 10) | 4 (3, 7) |
| Day 2 | 14 (10, 23) | 4 (3, 6) | 4 (3, 7) | 4 (3, 7) | 5 (2, 5) |
| Day 29 | 4 (1, 6) | 4 (3, 6) | 3 (1, 7) | 2 (1, 6) | 1 (1, 3) |
| Day 85 | 4 (2, 8) | 3 (1, 7) | 3 (1, 4) | 1 (1, 3) | 1 (1, 4) |
| Day 169 | 5 (3, 8) | 3 (1, 6) | 4 (1, 5) | 2 (1, 5) | 1 (1, 2) |

The foregoing data indicates that in comparison with leuprolide (Lupron Depot®), abarelix depot (especially at higher dosages) demonstrates a different effect on FSH manifested as a more rapid reduction in FSH levels and greater maintenance of FSH suppression.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating hormone refractory prostate cancer in a male subject, comprising administering to a subject a gonadotropin releasing hormone (GnRH) antagonist suitable for in vivo administration and able to reduce both plasma follicle stimulating hormone (FSH) and luteinizing hormone (LH) levels in a subject in an amount or in a formulation effective to reduce plasma FSH levels in the subject to a symptom alleviating level, wherein the GnRH antagonist is a decapeptide or a nonapeptide compound having a D-asparagine, an L-asparagine, a D-glutamine, or an L-glutamine at a position corresponding to position 6 of naturally occurring GnRH, or a pharmaceutically acceptable salt thereof, thereby treating an FSH related condition in the subject.

2. The method of claim 1, wherein the symptom alleviating level is about 1–4 mIU/ml.

3. The method of claim 1, wherein the symptom alleviating level is about 1 mIU/ml or less.

4. The method of claim 1, wherein the symptom alleviating level is about 2 mIU/ml or less.

5. The method of claim 1, wherein the symptom alleviating level is about 3 mIU/ml or less.

6. The method of claim 1, wherein the symptom alleviating level is about 4 mIU/ml or less.

7. A method for reducing follicle stimulating hormone (FSH) levels in a male subject to treat hormone refractory prostate cancer comprising administering to the subject a gonadotropin releasing hormone (GnRH) antagonist suitable for in vivo administration and able to reduce both FSH and luteinizing hormone (LH) levels in a subject in an amount or in a formulation effective to reduce plasma FSH in the levels subject, wherein the GnRH antagonist is a decapeptide or a nonapeptide compound having a D-asparagine, an L-asparagine, a D-glutamine, or an L-glutamine at a position corresponding to position 6 of naturally occurring GnRH, or a pharmaceutically acceptable salt thereof, thereby reducing FSH levels in the subject.

8. The method of claim 1, or claim 7, wherein in the GnRH antagonist has an $ED_{50}$ for histamine release in a standard in vitro histamine release assay of at least 3 μg/ml.

9. The method of claim 1 or claim 7, wherein the GnRH antagonist has an $ED_{50}$ for histamine release in a standard in vitro histamine release assay of at least 5 μg/ml.

10. The method of claim 1 or claim 7, wherein the GnRH antagonist has an $ED_{50}$ for histamine release in a standard in vitro histamine release assay of at least 10 μg/ml.

11. The method of claim 1 or 7, wherein the GnRH antagonist is a decapeptide.

12. The method of claim 1 or 7, wherein the GnRH antagonist is a nonapeptide.

13. The method of claim 1 or 7, wherein the GnRH antagonist is a peptide compound comprising a structure:

A-B-C-D-E-F-G-H-I-J wherein
A is pyro-Glu, Ac-D-Nal, Ac-D-Qal, Ac-Sar, or Ac-D-Pal, or an analogue thereof;
B is His or 4-Cl-D-Phe, or an analogue thereof;
C is Trp, D-Pal, D-Nal, L-Nal-D-Pal(N—O), or D-Tip, or an analogue thereof;
D is Ser, or an analogue thereof;
E is N-Me-Ala, Tyr, N-Me-Tyr, Ser, Lys(iPr), 4-Cl-Phe, His, Asn, Met, Ala, Arg or Ile, or an analogue thereof;
F is D-Asn or D-Gln;
G is Leu or Trp, or analogue thereof;
H is Lys(iPr), Gln, Met, or Arg, or an analogue thereof;
I is Pro, or an analogue thereof; and
J is Gly-NH$_2$ or D-Ala-NH$_2$, or an analogue thereof;
or a pharmaceutically acceptable salt thereof.

14. The method of claim 1 or 7, wherein the GnRH antagonist is a peptide compound comprising a structure:

A-B-C-D-E-F-G-H-I-J wherein
A is pyro-Glu, Ac-D-Nal, Ac-D-Qal, Ac-Sar, or Ac-D-Pal, or an analogue thereof;
B is His or 4-Cl-D-Phe, or an analogue thereof;
C is Trp, D-Pal, D-Nal, L-Nal-D-Pal(N—O), or Trp, or an analogue thereof;
D is Ser, or an analogue thereof;
E is N-Me-Ala, Tyr, N-Me-Tyr, Ser, Lys(iPr), 4-Cl-Phe, His, Asn, Mer, Ala, Arg or Ile, or an analogue thereof;
F is D-Asn;
G is Leu or Trp, or an analogue thereof;
H is Lys(iPr), Gln, Met, or Arg, or an analogue thereof;
I is Pro, or an analogue thereof; and
J is Gly-NH$_2$ or D-Ala-NH$_2$, or an analogue thereof;
or a pharmaceutically acceptable salt thereof.

15. The method of claims 1 or 7, wherein the GnRH antagonist is a peptide compound comprising a structure:

Ac-D-Nal-4-Cl-D-Phe-D-Pal-Ser-N-Me-Tyr-D-Asn-Leu-Lys(iPr)-Pro-D-Ala-NH$_2$;

or pharmaceutically acceptable salt thereof.

16. The method of claim 1 or 7, wherein the GnRH antagonist is a peptide compound comprising a structure:

Ac-D-Nal-4-Cl-D-Phe-D-Pal-Ser-Tyr-D-Asn-Leu-Lys(iPr)-Pro-D-Ala-NH$_2$;

or a pharmaceutically acceptable salt thereof.

17. The method of claim 1 or 7, wherein the GnRH antagonist is administered to the subject using a sustained-release formulation.

18. The method of claim 17, wherein the sustained-release formulation of GnRH antagonist comprises a solid ionic complex of a GnRH antagonist and a carrier macromolecule, wherein the carrier and GnRH antagonist used to form the complex are combined at a weight ratio of carrier antagonist of 0.5:1 to 0.1.1.

19. The method of claim 1 or 7, wherein the GnRH antagonist is administered at a dosage of about 5–500 µg/kg/day.

20. The method of claim 1 or 7, wherein the GnRH antagonist is administered at a dosage of about 10–400 µg/kg/day.

21. The method of claims 1 or 7, wherein the GnRH antagonist is administered at a dosage of about 10–100 µg/kg/day.

22. The method of claim 1 or 7, wherein the subject is a mammal.

23. The method of claim 22, wherein the mammal is a human.

24. A method for treating hormone refractory prostate cancer in a male subject, comprising administering to a subject a gonadotropin releasing hormone (GnRH) antagonist comprising Ac-D-Nal-4-Cl-D-Phe-D-Pal-Ser-Tyr-D-Asn-Leu-Lys(iPr)-Pro-D-Ala-NH$_2$ in an amount or in a formulation effective to reduce plasma follicle stimulating hormone (FSH) levels in the subject to a symptom alleviating level, thereby treating hormone refractory prostate cancer in the subject.

25. A method for treating hormone refractory prostate cancer in a male subject, comprising administering to a subject a gonadotrophin releasing hormone (GnRH) antagonist comprising Ac-D-Nal-4-Cl-D-Phe-D-Pal-Ser-N-Me-Tyr-D-Asn-Leu-Lys(iPr)-Pro-D-Ala-NH$_2$ in an amount or in a formulation effective to reduce plasma follicle stimulating hormone (FSH) levels in the subject to a symptom alleviating lelvel, thereby treating hormone refractory prostate cancer in the subject.

26. The method of anyone of claim 24 or 25 wherein said plasma FSH level is 2 mIU/ml or less for a period of at least 29 days.

27. The method of anyone of claim 24 or 25 wherein said plasma FSH level is 2 mIU/ml or less for a period of at least 57 days.

28. A method for treating hormone refractory prostate cancer in a male subject, comprising administering to a subject a gonadotropin releasing hormone (GnRH) antagonist suitable for in vivo administration and able to reduce both plasma follicle stimulating hormone (FSH) and luteinizing hormone (LH) levels in a subject in an amount or in a formulation effective to reduce plasma FSH levels in the subject to a symptom alleviating level, wherein the GnRH antagonist is a peptide compound comprising a structure:

A-B-C-D-E-F-G-H-I-J wherein

A is pyro-Glu, Ac-D-Nal , Ac -D-Qal, Ac-Sar, or Ac-D-Pal, or an analogue thereof;

B is His or 4-Cl-D-Phe, or an analogue thereof;

C is Trp, D-Pal, D-Nal, L-Nal-D-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Mer, Ala, Arg or Ile, or an analogue thereof;

F is D-Asn;

G is Leu or Trp, or an analogue thereof;

H is Lys(iPr), Gln, Met, or Arg, or an analogue thereof;

I is Pro, or an analogue thereof; and

J is Gly-NH$_2$ or D-Ala-NH$_2$, or an analogue thereof;

or a pharmaceutically acceptable salt thereof, thereby treating hormone refractory prostate cancer in the male subject.

29. A method for reducing follicle stimulating hormone (FSH) levels in a male subject to treat hormone refractory prostate cancer comprising administering to the subject a gonadotropin releasing hormone (GnRH) antagonist suitable for in vivo administration and able to reduce both FSH and luteinizing hormone (LH) levels in a subject in an amount or in a formulation effective to reduce plasma FSH levels in the subject, wherein the GnRH antagonist is a peptide compound comprising a structure:

A-B-C-D-E-F-G-H-I-J wherein

A is pyro-Glu, Ac-D-Nal , Ac -D-Qal, Ac-Sar, or Ac-D-Pal, or an analogue thereof;

B is His or 4-Cl-D-Phe, or an analogue thereof;

C is Trp, D-Pal, D-Nal, L-Nal-D-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Mer, Ala, Arg or Ile, or an analogue thereof;

F is D-Asn;

G is Leu or Trp, or an analogue thereof;

H is Lys(iPr), Gln, Met, or Arg, or an analogue thereof;

I is Pro, or an analogue thereof; and

J is Gly-NH$_2$ or D-Ala-NH$_2$, or an analogue thereof;

or a pharmaceutically acceptable salt thereof, thereby reducing FSH levels in the male subject.

* * * * *

UNITED STATES PATENT AND TRADEMARK OFFICE
CERTIFICATE OF CORRECTION

PATENT NO. : 7,109,171 B2
APPLICATION NO. : 09/793669
DATED : September 19, 2006
INVENTOR(S) : Marc B. Garnick et al.

It is certified that error appears in the above-identified patent and that said Letters Patent is hereby corrected as shown below:

In claim 1, at column 23, lines 54-55, "thereby treating an FSH related condition in the subject" should read as -- thereby treating hormone refractory prostate cancer in the subject --;

In claim 13, at column 24, line 34, "D-Tip," should read as -- D-Trp, --;

In claim 14, at column 24, line 60, "Mer," should read as -- Met, --;

In claim 18, at column 25, line 21, "carrier antagonist" should read as -- carrier:antagonist --;

In claim 18, at column 25, line 22 "0.1.1" should read as -- 0.1:1 --;

In claim 28, at column 26, line 12, "Ac-D-Nal , Ac –D-Qal," should read as -- Ac-D-Nal, Ac– D-Qal, --;

In claim 28, at column 26, line 16, the second usage of "Trp," should read as -- D-Trp, --;

In claim 28, at column 26, line 20, "Mer," should read as -- Met, --;

In claim 28, at column 26, line 21, "F is D-Asn" should read as --F is D-Asn or D-Gln; --

In claim 29, at column 26, line 42, "Ac-D-Nal , Ac –D-Qal," should read as -- Ac-D-Nal, Ac– D-Qal, --;

In claim 29, at column 26, line 46, the second usage of "Trp," should read as -- D-Trp, --;

In claim 29, at column 26, line 50, "Mer," should read as -- Met, --; and

UNITED STATES PATENT AND TRADEMARK OFFICE
CERTIFICATE OF CORRECTION

PATENT NO. : 7,109,171 B2
APPLICATION NO. : 09/793669
DATED : September 19, 2006
INVENTOR(S) : Marc B. Garnick et al.

It is certified that error appears in the above-identified patent and that said Letters Patent is hereby corrected as shown below:

In claim 29, at column 26, line 51, "F is D-Asn" should read as -- F is D-Asn or D-Gln; --.

Signed and Sealed this

Thirteenth Day of February, 2007

JON W. DUDAS
*Director of the United States Patent and Trademark Office*